United States Patent [19]
Johnson et al.

[11] Patent Number: 5,866,801
[45] Date of Patent: Feb. 2, 1999

[54] UNIVERSAL PENETRATION TEST APPARATUS WITH FLUID PENETRATION SENSOR

[75] Inventors: Phillip W. Johnson, Rochester, Minn.; Joseph F. Stampfer; Orvil D. Bradley, both of Santa Fe, N. Mex.

[73] Assignee: Regents of the University of California, Oakland, Calif.

[21] Appl. No.: 664,533

[22] Filed: Jun. 17, 1996

Related U.S. Application Data

[63] Continuation-in-part of Ser. No. 493,277, Jun. 21, 1995, Pat. No. 5,633,453, which is a continuation-in-part of Ser. No. 291,745, Aug. 17, 1994, Pat. No. 5,467,639, which is a continuation of Ser. No. 004,839, Jan. 19, 1993, abandoned.

[51] Int. Cl.$^6$ .................................................. G01N 15/08
[52] U.S. Cl. .................................................................. 73/38
[58] Field of Search ............................... 73/38, 64.47, 78, 73/81, 82, 84, 85, 818, 820, 821

[56] References Cited

U.S. PATENT DOCUMENTS

| | | |
|---|---|---|
| 1,232,782 | 7/1917 | Field ............................................. 73/81 |
| 2,078,296 | 4/1937 | Vadner ................................. 73/821 X |
| 3,028,755 | 4/1962 | Carter ........................................... 73/38 |
| 3,443,423 | 5/1969 | Lou Ma . |
| 3,504,527 | 4/1970 | Marshall ...................................... 73/38 |
| 3,577,767 | 5/1971 | Stedile ........................................ 73/38 |
| 4,050,995 | 9/1977 | Bredeweg . |
| 4,140,008 | 2/1979 | Golembeck et al. . |
| 4,194,041 | 3/1980 | Gore et al. . |
| 4,214,320 | 7/1980 | Belkin . |
| 4,310,057 | 1/1982 | Brame . |
| 4,327,731 | 5/1982 | Powell . |
| 4,344,999 | 8/1982 | Gohlke . |
| 4,382,990 | 5/1983 | Coates . |
| 4,385,517 | 5/1983 | Sorce et al. . |
| 4,448,204 | 5/1984 | Lichtenstein . |
| 4,454,055 | 6/1984 | Richman et al. . |

(List continued on next page.)

FOREIGN PATENT DOCUMENTS

| | | |
|---|---|---|
| 1168469 | 6/1984 | Canada ......................................... 73/38 |
| 59-200941 | 11/1984 | Japan . |
| 60-88350 | 5/1985 | Japan . |
| 63-252232 | 10/1988 | Japan . |
| 577434 | 10/1977 | U.S.S.R. ..................................... 73/38 |
| 1564521 | 5/1990 | U.S.S.R. ..................................... 73/38 |

OTHER PUBLICATIONS

"Measuring Water Resistance of Leather", May 1960, p. 81.
Bernard Miller, "Experimental Aspects of Fiber Wetting and Liquid Movement Between Fibers", Chapter IV, Textile Research Institute, Princeton, New Jersey, USA pp. 121–147.
"Personal Protective Equipment", *Federal Register Rules and Regulations*, vol. 56, No. 235, Dec. 6, 1991, pp. 64124–64139.
Norman W. Henry, III, "Biological Resistant Clothing–Standards in the Making", *ASTM Standardization News*, May 1992, pp. 32–33.
Brochure for "F 903 Penetration Test Apparatus", Wilson Road Machine Shop, 1170 Wilson Road, Rising Sun, Maryland USA 21911 1992, 4 pp. .
Draft of "Standard Test Method for Resistance of Protective Clothing Materials To Synthetic Blood", Task Group No. ASTM F23.40.01, Draft No. 5, ASTM, May 1992, 18 pp. .

(List continued on next page.)

*Primary Examiner*—Daniel S. Larkin
*Attorney, Agent, or Firm*—Gemma Morrison Bennett; David G. Schmaltz; Merchant, Gould, Smith, Edell, Welter & Schmidt

[57] ABSTRACT

A universal penetration test apparatus for measuring resistance of a material to a challenge fluid. The apparatus includes a pad saturated with the challenge fluid. The apparatus includes a compression assembly for compressing the material between the pad and a compression member. The apparatus also includes a sensor mechanism for automatically detecting when the challenge fluid penetrates the material.

11 Claims, 22 Drawing Sheets

U.S. PATENT DOCUMENTS

| | | |
|---|---|---|
| 4,495,795 | 1/1985 | Gupta . |
| 4,565,089 | 1/1986 | Arciszewski et al. . |
| 4,678,757 | 7/1987 | Rapkin et al. . |
| 4,747,685 | 5/1988 | Suzuki . |
| 4,820,051 | 4/1989 | Yanagisawa et al. . |
| 4,896,418 | 1/1990 | Yearsley . |
| 4,918,981 | 4/1990 | Gore . |
| 4,948,561 | 8/1990 | Hinckley et al. . |
| 4,961,339 | 10/1990 | Kleis et al. . |
| 5,073,482 | 12/1991 | Goldstein ................................ 73/38 X |
| 5,216,727 | 6/1993 | Vakhshoori et al. . |
| 5,265,177 | 11/1993 | Cho et al. . |
| 5,301,201 | 4/1994 | Dutta et al. . |
| 5,365,793 | 11/1994 | Terrel et al. . |
| 5,467,639 | 11/1995 | Johnson ....................................... 73/38 |

OTHER PUBLICATIONS

Jerry R. Nelson, "Final Report Elbo Lean ΦX1 Challenge Test Protocol No. 900543–1", Nelson Laboratories, Inc., Salt Lake City Utah, USA, 84117 Dec. 13, 1990, pp. 1–13.

K.W. Altman et al., "Transmural Surgical Gown Pressure Measurements In The Operating Theater", *American Journal of Infection Control*, vol. 19, No. 3, Jun. 1991, pp. 147–155.

*Popular Science*, Jul. 1994, Mariette DiChristina, p. 32, R&D Self–Focusing Lasers article.

Peter L. Brown, "Protective Clothing for Health Care Workers: Liquidproofness Versus Microbilogical Resistance", Performance of Protective Clothing: Fourth Vol. ASTM STP 1133, 1992.

Jeffrey W. Smith and Ronald Lee Nichols, "Barrier Efficiency of Surgical Gowns—Are We Really Protected From Our Patients'Pathogens?" Archives of Surgery, Jun. 1991, vol. 126, pp. 756–763.

"Standard Test Method for Resistance of Protective Clothing Materials to Penetration by Liquids", ASTM Designation F 903–90, ASTM, Dec. 1990, 10 pp. .

"Emergency Standard Test Method for Resistance of Protective Clothing Materials to Synthetic Blood", ASTM Designation ES 21–92, ASTM, Nov. 1992, 4 pp.

UNIVERSAL PENETRATION TEST APPARATUS WITH FLUID PENETRATION SENSOR

This application is a continuation-in-part of corresponding U.S. patent application Ser. No. 08/493,277 which was filed on Jun. 21, 1995, now U.S. Pat. No. 5,633,453. U.S. patent application Ser. No. 08/493,277 is a continuation-in-part of corresponding U.S. patent application Ser. No. 08/291,745 which was filed on Aug. 17, 1994 and issued as U.S. Pat. No. 5,467,639 on Nov. 21, 1995. U.S. patent application Ser. No. 08/291,745 is a file wrapper continuation of U.S. patent application Ser. No. 08/004,839 which was filed on Jan. 19, 1993 and is presently abandoned.

This invention was made with government support under Contract No. W-7405-ENG-36 awarded by the U.S. Department of Energy. The government has certain rights in the invention.

FIELD OF THE INVENTION

The present invention relates to test apparatus and methods for measuring the resistance of materials; e.g., protective fabrics, to penetration by fluids, pathogens and other fluid/fluid vapor transmissible particles.

BACKGROUND OF THE INVENTION

The permeability of a material relates to the ability of a fluid and fluid transmissible particles to penetrate the material. Different materials have different permeabilities. Some materials are impervious to some fluids, that is, they are unable to be penetrated by those fluids. Some materials are pervious to various fluids. Of course, most materials are semi-impervious to various fluids.

In an effort to protect workers who are exposed to bloodborne pathogens or other infectious materials at work, the Occupational Safety and Health Agency (OSHA) has set requirements for the penetrability of protective clothing by bloodborne pathogens and/or other infectious materials; e.g., the Bloodborne Pathogen Standard of Dec. 6, 1991.

To determine the permeability of various materials, researchers have been trying to find a simple, universal test method and apparatus. One simple pass/fail penetration test is referred to as the Elbow Lean Test. In this test, a conventional rubber stamp ink pad is saturated with a challenge fluid; that is, the fluid with which the permeability of particular material is to be tested. The test material is then placed over the pad with the outside down against and in contact with the stamp pad. A person then leans on the pad with their elbow. If fluid is detected on the inside surface of the material, the material fails the test. If no fluid is detected, the material passes the test. This is a very general pass/fail test as the force exerted by one's elbow may vary greatly; e.g., twenty to seventy pounds.

Recently, there has been substantial concern over the safety of healthcare professions and others who come in professional contact with blood that may contain pathogens such as hepatitis B virus (HBV) and human immunodeficiency virus (HIV), as well as other infectious materials.

In some penetration tests, the permeability of various pathogens or other fluid transmitted particles is being tested. In these cases, alternative detection means other than visual detection is used to determine if penetration has occurred. For example, chemical detectors, radioactive detectors, etc. might be used. In many cases alternative detectors are used where the fluid is colorless and cannot be visually detected. If the fluid is colorless, dyes or other coloring agents can be added to aid in the visual detection process.

Material penetration testing is replete with testers which use pressurized hydrostatic or fluid impact penetration mechanisms to demonstrate material liquid penetration resistance. These tests and testers include the following: INDA Water Spray Test IST 80.1-70 (R82), INDA Impact Penetration Test IST 80.5-70 (R82), INDA Hydro Pressure Test IST 80.6-70 (R82), INDA Saline Repellency Test IST 80.7-70 (R82), AATCC Water Resistance: Suter Hydrostatic Pressure Test 127-1985, AATCC Spray Rating Test 22-1985, AATCC Rain Test 35-1985, Federal Gov. Water Resistance of Coated Cloth; High Range, Hydrostatic Pressure Method, ASTM Mullen Hydrostatic test D751, ASTM Standard Test Method For Resistance of Protective Clothing To Penetration By Liquids F903-90, ASTM Emergency Standard Test Method for Resistance Of Protective Clothing Materials To Synthetic Blood F23.40.01, and ASTM Emergency Standard Test Method For Resistance Of Protective Clothing Materials To Penetration By Bloodborne Pathogens Using Viral Penetration As A Test System F23.40.02.

The testers used in these tests are typically complicated in design, cumbersome to set up, time consuming to use, difficult to clean, semi-portable, not suitable for field use, expensive, and based on subjecting test materials to contained hydrostatic pressures which are not representative of actual use conditions experienced by wearers of protective clothing where free flowing fluids on the outer surfaces of a material are momentarily pressurized against the clothing and skin of the wearer by fingers, elbows, and other objects. A good example of this type of testing is American Society for Testing and Materials (ASTM) F 903-90 standard test method for resistance of protective clothing materials to penetration by liquids. This test requires that the material to be tested is mounted in a test cell which in turn is attached to an air pressure line. The challenge fluid is then exposed to a predetermined air pressure for a predetermined period of time.

This contained hydrostatic pressure method also unnaturally expands, stretches, and pulls apart the material structure thereby causing failure of the liquid/pathogen barrier and avoidable negative results in both visible liquid and pathogen penetration tests. Therefore, the contained hydrostatic pressure method is too rigorous for 90% of the protective products market and unnecessarily expensive for manufacturers and consumers.

The present invention solves many of the problems associated with the prior art.

SUMMARY OF THE INVENTION

The present invention relates to an apparatus and method for testing the penetration of sheet material by fluids and fluid transmitted particles and pathogens.

Throughout this description reference will be made to fluid penetration of the test material. This will refer to both the fluid itself and/or particles/pathogens contained therein which are often referred to as the challenge substance. The use of the term fluid refers to both gas/vapor and liquid substances.

One embodiment of the invention provides a universal penetration test apparatus of simple and inexpensive design and which is simple to set up and easy to use.

One embodiment of the invention provides a universal penetration test apparatus which accurately defines the range of pressures that a test material will withstand, before penetration, by a test fluid.

One embodiment of the invention provides universal penetration test apparatus and methods which can be used in a minimum amount of time.

One embodiment of the invention provides universal penetration test apparatus which is easily cleanable after use.

One embodiment of the invention provides a universal penetration test apparatus which is small and highly portable.

One embodiment of the invention provides universal penetration test apparatus and methods which are suitable for laboratory and field use by both technical and non-technical individuals.

One embodiment of the invention provides universal penetration test apparatus which can be used to test most types of materials to penetration by fluids. One embodiment is particularly suited for testing penetration of bloodborne pathogens.

One embodiment of the invention provides universal penetration test apparatus which can be used for testing any type of material which is designed to prevent the penetration of fluids.

One embodiment of the invention provides universal penetration test apparatus which simulates actual use conditions by applying non-contained hydrostatic and mechanical pressures to the surface of a test material.

One embodiment of the invention provides universal penetration test apparatus which causes minimal deflection, expansion, stretching, or pulling apart of the test material structure.

One embodiment of the invention provides universal penetration test apparatus which allows easy viewing of the surface area being tested.

One embodiment of the invention provides universal penetration test apparatus which uses a minimal amount of weight in proportion to the surface area of the apparatus contact point to achieve failure of the test material.

One embodiment of the invention traps, contains and creates hydrostatic pressure without external air or liquid supply lines.

In one embodiment, a universal penetration and test apparatus includes a dense latex foam pad with the challenge fluid to prevent the challenge fluid from moving rapidly and perpendicularly/radially away from the pressure point before the challenge fluid penetrates the test material. In other words, the path of least resistance is through the test material.

In one embodiment, a universal penetration and test apparatus comprises a tray containing the fluid saturated latex foam pad so as to prevent loss of the fluid from the test site.

In one embodiment the present invention comprises a universal material penetration tester kit including (1) a plurality of weights in varying sizes with center holes, (2) a hollow sleeve, preferably made of metal or plastic, insertable into the center holes of the weights and having a protruding flange on its outer surface to support he weights, (3) a solid rod of clear material such as Plexiglas with a protruding flange near its base to support the sleeve, and with a rubber O-ring just above the flange to prevent the sleeve and rod from separating, (4) a collapsible frame with a center hole to support the rod and sleeve in an upright position, (5) a highly absorbent material, such as a sponge or dense latex foam or similar material, to contain a fluid or other substance often referred to as a challenge fluid or substance, and (6) a leak proof tray to hold the sponge.

In one embodiment of the invention an optional absorbent paper is used with a plastic coating on one side to protect the base of the rod from contamination by the challenge fluid or other substance in the sponge.

One embodiment of the invention provides a tester apparatus which eliminates the need for the frame, rod and sleeve member.

One embodiment of a test method in accordance with the principles of the present invention includes the following steps:

The sponge is placed in the tray, a challenge fluid or other challenge substance is applied to the sponge until it is saturated, a test material is placed with its outer surface down against the sponge, a piece of absorbent paper larger than the base of the plastic rod is placed on top of the test material with the absorbent side against the test material, the frame is opened and centered over the sample, the sleeve is placed down over the rod until it contacts the flange at the end of the rod and is locked in place by the pressure of the O-ring on the rod, a weight is then placed down onto the sleeve until it contacts the sleeve flange, and the rod/sleeve assembly is placed through the frame supporting hole until the rod base rests upon the paper. The test dynamics can be viewed through the end of the transparent rod. If the challenge fluid or other challenge substance does not penetrate the sample, additional weights are added until failure occurs, which is evident by the appearance of the challenge fluid or challenge substance on the absorbent paper as seen through the upper end of the rod.

Appearance of the challenge fluid or challenge substance in the absorbent paper under the rod base constitutes a failure of the test material at a specific pressure, e.g., pounds per square inch. The applied pressure, in psi, on the test material is then determined by dividing the amount of the total weight resting on the test material by the surface area of the rod base. Therefore, by increasing or decreasing the weight and the diameter of the rod base in contact with the test material, more or less pressure can be applied to the test material. This quantitative and qualitative analysis of samples can be used for selecting materials which can withstand penetration of specific fluids and other substances at the greatest pressure, and, can be used as a product quality assurance tool.

In one embodiment, the rod base has a surface area of one square inch such that the pressure in pounds per square inch can be determined by simply determining the total weight in pounds. Likewise, other embodiments of the invention might be similarly sized for other units of measurement and/or sized so as to allow simple calculation of the pressure by the use of whole number factors.

Another embodiment of the invention comprises using a challenge fluid or challenge substance which may penetrate the sample without visible evidence. Confirmation of penetration can then be determined using standard laboratory procedures. For example, chemical detectors, radioactive detectors, etc. might be used. The fluid might also be colored with a suitable dye or colorant.

Yet another embodiment of the invention comprises weighing the absorbent paper before and after testing two different samples to determined which sample allowed the least amount of challenge liquid or material to pass through.

Control of fluid dynamics is also very important in obtaining valid results. If the test apparatus and methods are used without a sponge of the right density and thickness, the challenge fluid will move horizontally away from the pressure point at a velocity which is directly proportionate to the weight applied and the speed with which the weight is applied. The density and thickness of the sponge, in one embodiment, is selected to keep the challenge liquid (synthetic blood) under the sample long enough for the weight bearing rod to create a hydrostatic pressure between the liquid and the test material.

Another embodiment of the present invention includes a rod base having concentric circles of varying widths cut at different depths and at different distances apart with the inner most concentricity having the greatest depth; all of which combined, however, do not equal the combined thickness of the sponge, test material and paper. The effect of the concentric rings is to force the liquid toward the center which has the lowest pressure until the final peak pressure is applied by the weight bearing rod.

Another embodiment of the present invention includes a rod with a threaded end which screws into a base which serves as both the contact surface against the test material and as the support for the weight which slide down over the rod and rest against the upper surface of the base, thereby eliminating the need for the sleeve and the supporting frame.

Another embodiment of the present invention includes conical free-standing weights of different sizes with the top and bottom of each weight serving as a contact surface against the test material, thereby eliminating the sleeve and allowing for greater variations in applied pressures.

Another embodiment of the present invention includes spherical weights of different sizes. This embodiment eliminates the need for the rod, shaft and stand, but prevents viewing the test in progress.

Another embodiment of the present invention includes a rod having a base end defining concentric circles of varying widths cut at different depths with an innermost concentricity having the greatest depth. A passageway preferably extends from the innermost concentricity through the length of the rod for preventing pressure build up at the innermost concentricity of the rod.

Another embodiment of the present invention provides a universal material penetration test apparatus which minimizes the opportunity for operator error.

Another embodiment of the present invention provides a universal material penetration test apparatus which provides reproducible and accurate test results.

Another embodiment of the present invention provides a universal material penetration test apparatus that minimizes the number of test variables by providing an improved compression assembly.

Another embodiment of the present invention provides a universal penetration test apparatus including a screw assembly for compressing a test material between a pad and a base end of a rod.

Another embodiment of the present invention provides a universal penetration test apparatus having a weighing indicator for precisely monitoring and controlling a pressure exerted on a test material.

Another embodiment of the present invention provides a universal penetration test apparatus having a sensor for automatically detecting when a test fluid penetrates a test material. The test apparatus preferably includes a compression assembly for compressing the test material between a test head and the test fluid. The sensor is preferably provided on the test head of the compression assembly. The test apparatus also preferably includes a weight indicator for measuring the mechanical pressure exerted upon the test material by the test head. When fluid penetration is detected by the sensor, the compression assembly is preferably deactivated and the weighing indicator preferably displays and prints out the pressure at which penetration occurred.

These and various other advantages and features of novelty which characterize the invention are pointed out with particularity in the claims annexed hereto and forming a part hereof. However, for a better understanding of the invention, its advantages, and objects obtained by its use, reference should be had to the drawing which forms a further part hereof, and to the accompanying descriptive matter, in which there is illustrated and described a preferred embodiment of the invention.

BRIEF DESCRIPTION OF THE DRAWINGS

In the drawings, in which like reference numerals and letters generally indicate corresponding parts throughout the several views.

DETAILED DESCRIPTION OF AN EMBODIMENT OF THE INVENTION

Figure 1:
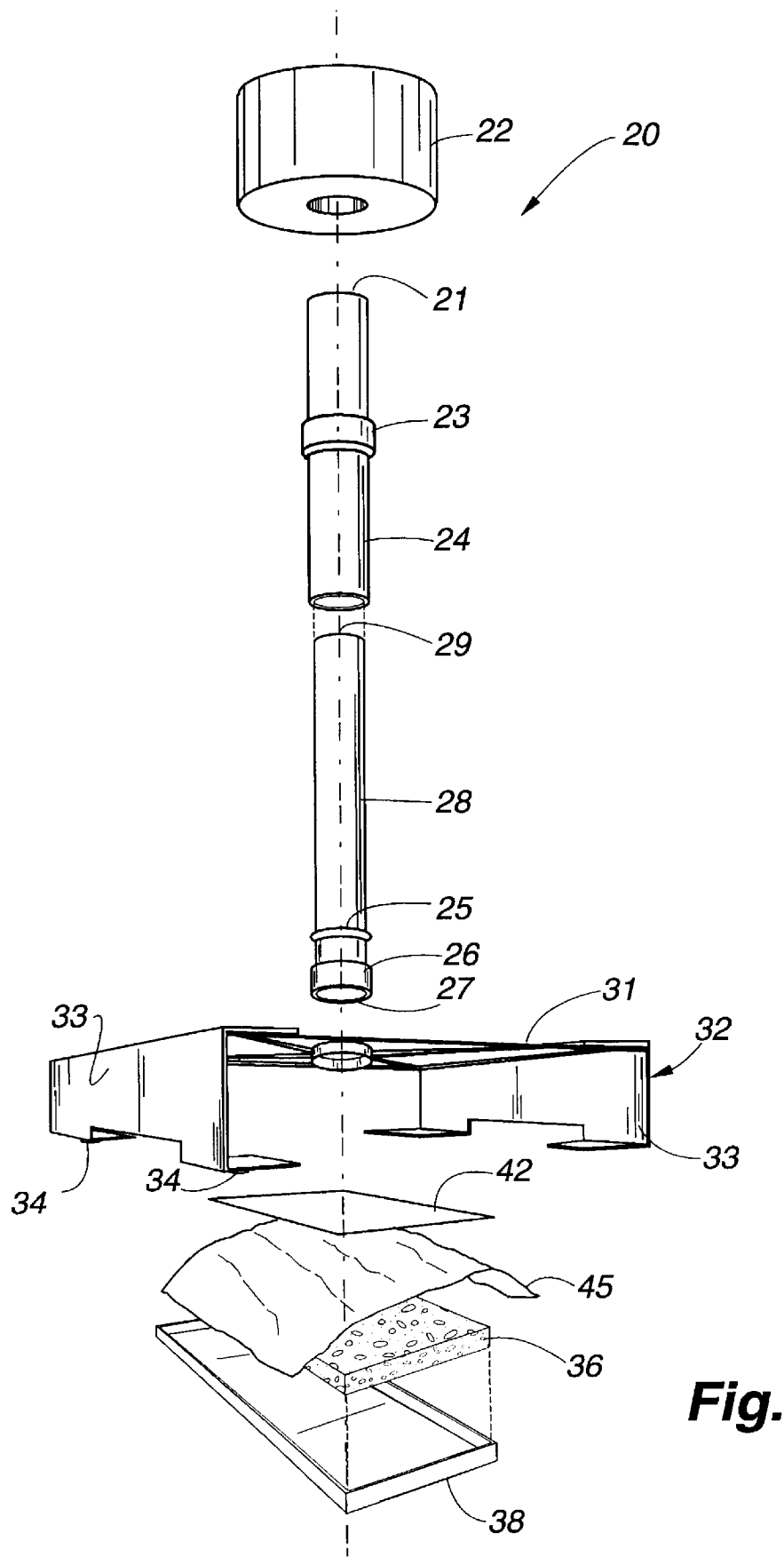
FIG. 1 is an exploded view of an embodiment of a universal penetration test apparatus generally in accordance with the principles of the present invention.
Figure 2:
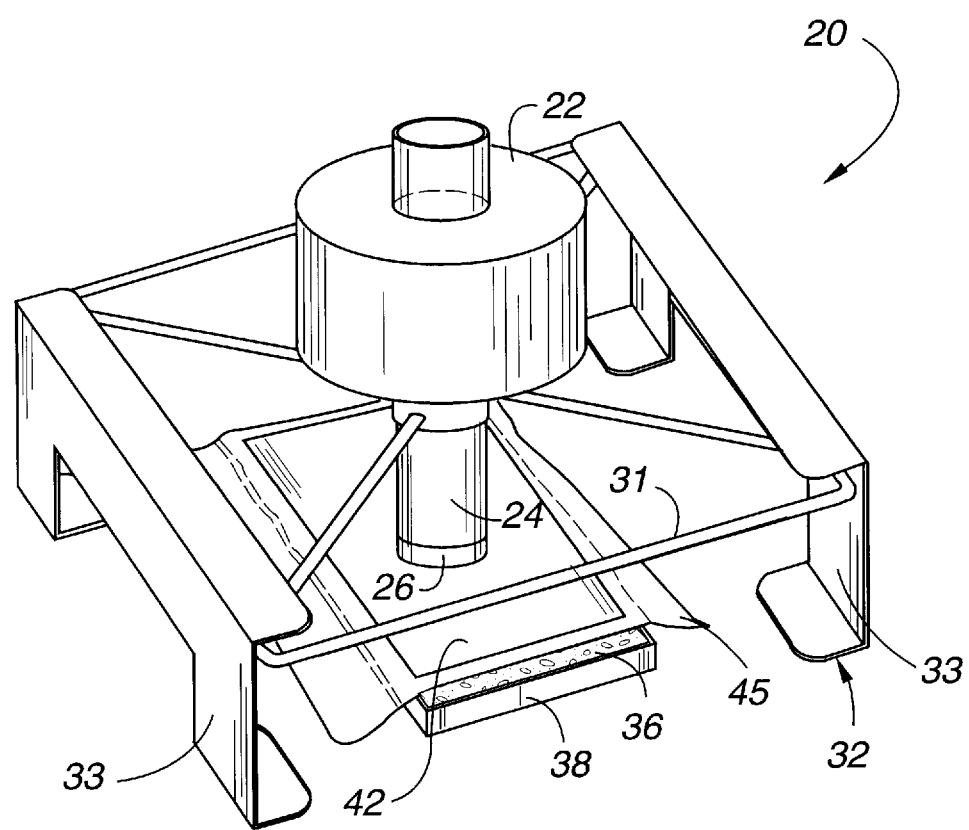
FIG. 2 is a view of the universal penetration test apparatus shown in FIG. 1, in its testing position.

Referring to FIGS. 1 and 2, there is shown an embodiment of a universal material penetration tester, designated by the reference numeral 20, generally in accordance with the principles of the present invention.

The embodiment shown in FIGS. 1 and 2 illustrates a universal material penetration tester 20, including a hollow sleeve 24, preferably made of metal or plastic. The sleeve 24 includes a top end 21. In addition, the sleeve 24, as shown, includes a flange 23 proximate the mid portion of the sleeve 24. A weight 22 is shown disposed for slidable insertion onto the end of the sleeve 24. Although not shown, a plurality of weights 22 might be placed on the sleeve 24. The flange 23 supports the weight 22 on the sleeve. It will be appreciated that the flange might be integral to the sleeve or suitably positioned thereon by use of suitable attachment mechanisms such as threaded thumb screws or the like. A rod 28 of clear material such as plexiglas is slidably insertable into the sleeve 24. The rod 28 is shown as including a protruding flange 26 proximate its base end 27 for supporting the sleeve 24. An O-ring 25 disposed above the flange 26 assists in preventing the sleeve 24 and the rod 28 from separating. The sleeve 24 and rod 28 are slidably received in a collapsible frame assembly 32 having a center hole therein for assisting in supporting the rod 28 and sleeve 24 in an upright position. In the embodiment shown, the ends 21 and 29 of the sleeve and the rod, are substantially at the same height when the sleeve 24 is slid onto the rod 28. In some embodiments a plurality of sleeves and rods of various sizes might be provided with the tester apparatus.

The frame assembly 32 includes two U-shaped side members 33 and foot rests 34 protruding from the bottom of each of the U-shaped side members 33. A flat support member 31, having the hole disposed in the center thereof, interconnects the upper edges of the U-shaped side members 33. It will be appreciated that the frame assembly might take on any number of varying configurations and yet be in keeping with the principles of the invention. For example, to facilitate portability of the device, the frame assembly 32 might be collapsible and/or foldable onto itself.

Disposed in the frame assembly below the support member 31 is a highly absorbent material such as a sponge 36 of high density latex foam or similar material and a leak proof tray 38 for holding the sponge 36. The material 45 to be tested is shown disposed over the sponge 36. In this embodiment, an absorbent paper 42 such as a white absorbent laboratory paper with a plastic coating on a side facing the rod 28 is used to protect the base end 27 of the rod 28 from contamination by a challenge fluid or challenge substance which is contained in the sponge 36. It will be appreciated that the collapsible frame assembly and the sponge 36, the tray 38, the test material 45, and the absorbent paper 42, are supported by a suitable support surface such as a table top or the like not shown in the illustration.

Figure 3:
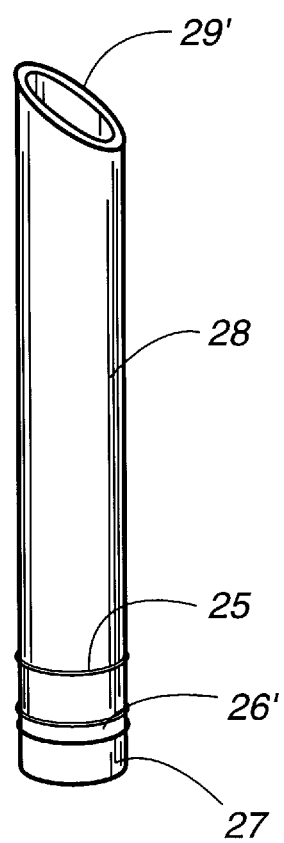
FIG. 3 is an alternate embodiment of the rod used in FIG. 1.

It will be appreciated that the various components of the embodiment illustrated in FIG. 1 might take on various alternative configurations and yet be in keeping with the principles of the invention. For example, as shown in FIG. 3, the rod 28 might have a flange 26' which does not extend all of the way to the base end 27. In addition, a top end 29' of the solid, transparent rod 28 is inclined at a 45 degree angle to facilitate viewing of the test material 45. In this embodiment, the end 29' of the rod 28 will preferably extend beyond the end 21 of the sleeve. As further illustrated in FIG. 4, the rod 28 might have concentric circles 27a–d, of varying widths, cut at different depths and at different distances apart, with the innermost concentric circle or center of the rod having the greatest depth. All of the concentric circles combined, however, do not equal the combined thickness of the sponge, test material and absorbent paper. In some embodiments of the invention, the absorbent paper 42 might not be used. Moreover, variations on the sponge 36/tray 38 might be used. These are but a few of the many examples of variations which might be made in the various components of the universal material penetration tester 20.

One method of testing, using the above-described embodiment, as shown in FIG. 1, includes placing the sponge 36 in the leak proof tray 38. A challenge fluid or other challenge substance is then applied to the sponge 36 until it is saturated. The test material 45 is then placed on the sponge 36, with its outer surface abutting the sponge 36. A piece of the absorbent paper 42, larger than the base end 27 of the rod 28, is placed on top of the test material 45 with the absorbent side against the test material 45. The plastic coating of the absorbent paper 42 is facing the rod 28. The frame assembly 32 is suitably placed over the assemblage of the plastic tray 38, the sponge 36, the test material 45, and the absorbent paper 42. The sleeve 24 is inserted over the rod 28 until it contacts the flange 26 proximate the end of the rod 28 and is retained in place by the force of the O-ring 25 on the rod 28. The sleeve 24 and rod 28 assembly is placed through the hole in the frame support member 31 until the base end 27 of the rod 28 rests on the absorbent paper 42. A weight 22 is then placed down onto the sleeve 24 until it contacts the sleeve flange 23 and is supported thereby. The user then views through a viewing end of the rod 28. If, within a predetermined period of time, e.g., five minutes, the challenge fluid or other challenge material does not penetrate the test material so as to be absorbed by the absorbent paper 42, additional weights are added until failure occurs, which is evident by the appearance of the challenge fluid or challenge material on the absorbent paper, as seen through the viewing end 29 of the rod 28.

In one embodiment, the test apparatus 20 will include a plurality of weights 22 with at least some of the weights 22 having a different weight. In one embodiment, one-half, one, tow, three, four and five pound weights 22 might be included. If used with a rod having a base end of one square inch, and a weight with the sleeve of one-half pound, this would allow measurements of up to sixteen pounds if all the weights were placed on the sleeve. If used with a rod having a base end of ¼ square inch, this would allow measurement up to sixty-four pounds. Up to one hundred twenty-eight pounds might be measured if a rod base end of ⅛ square inch were used. Of course, as opposed to using a smaller base end area, heavier weights might also be used.

Illustrated below is a weight/PSI conversion table with two different rod sizes; a first having a diameter of 1.128" or an area of 1" and a second having a diameter of 0.564" or an area of ¼".

| Applied Weight (lbs) | Rod #1 PSI | Rod #2 PSI | Applied Weight (lbs) | Rod #1 PSI | Rod #2 PSI |
| --- | --- | --- | --- | --- | --- |
| 1/16 | .0625 | .25 | 12.0 | 12.0 | 48.0 |
| 1/8 | .125 | .5 | 13.0 | 13.0 | 52.0 |
| 1/4 | .25 | 1.0 | 14.0 | 14.0 | 56.0 |
| 1/2 | .5 | 2.0 | 15.0 | 15.0 | 60.0 |
| 1.0 | 1.0 | 4.0 | 16.0 | 16.0 | 64.0 |
| 2.0 | 2.0 | 8.0 | 17.0 | 17.0 | 68.0 |
| 3.0 | 3.0 | 12.0 | 18.0 | 18.0 | 72.0 |
| 4.0 | 4.0 | 16.0 | 19.0 | 19.0 | 76.0 |
| 5.0 | 5.0 | 20.0 | 20.0 | 20.0 | 80.0 |
| 6.0 | 6.0 | 24.0 | 21.0 | 21.0 | 84.0 |
| 7.0 | 7.0 | 28.0 | 22.0 | 22.0 | 88.0 |
| 8.0 | 8.0 | 32.0 | 23.0 | 23.0 | 92.0 |
| 9.0 | 9.0 | 36.0 | 24.0 | 24.0 | 96.0 |
| 10.0 | 10.0 | 40.0 | 25.0 | 25.0 | 100.0 |
| 11.0 | 11.0 | 44.0 | 26.0 | 26.0 | 104.0 |

Legend:
Rod Tip    #1       #2
Diameter   1.128"   .564"
Area       1.00"    .25"

The weights might have differing lengths to reflect their different weight. In some embodiments, the collection of weights might include two or more weights 22 having the same weight, as well as weights 22 having different weights. In order to increase the total weight, additional weights 22 might be added onto the sleeve or the existing weight 22 might be replaced with one or more weights 22. In the embodiment shown, the weights 22 have a cylindrical shape, although other shapes might be used. In one embodiment, the rod base end 27 might have an area of one square inch and the weights have a diameter of four to six inches. The diameter of the weights ideally will not be too great so that the user can view the base end 27 of the rod 28 to make sure it is aligned properly with the surface of the absorbent paper 42. The weights might all have the same diameter or differ in diameter depending on their weight. In one embodiment the rod and sleeve might have a total weight of one-half pound.

Appearance of the challenge fluid or challenge material on the inner surface of the test material 45 under the rod 28 constitutes a failure of the test material 45 to a specific pressure. Such pressure might be measured in pounds per square inch, kg/cm2, kpa, etc. The applied weight, on the sample is then determined by dividing the amount of weight resting on the absorbent material 42 by the surface area of the rod base. Therefore, by increasing or decreasing the weight and the diameter of the rod base 27, in resting on the test material 24, more or less pressure can be applied to the test material's surface.

This qualitative analysis of samples can be used for selecting materials which can withstand penetration of specific challenge fluids and challenge substances such as blood, bloodborne pathogens at the greatest pressure, and as a product quality assurance tool. One of the many uses for such materials is in the design of protective clothing, such as gloves, arm shields, aprons, gowns, suits, hats, boots, masks and similar items which can limit human exposure to hazardous and biological liquids.

Another qualitative method consists of using a challenge fluid containing a pathogen or fluorescent dye which may penetrate the sample without visible evidence. Confirmation of pathogen penetration can then be determined using standard laboratory assay procedures or a black light.

Yet another quantitative method can also be used by weighing the absorbent paper before and after testing two different test materials to determine which test material allowed the least amount of challenge fluid or material to pass through.

Control of fluid dynamics is also very important in obtaining valid results. If the test apparatus and methods are used without a sponge of the right density and thickness, the challenge fluid will move horizontally away from the pressure point at a velocity which is directly proportionate to the weight applied and the speed with which the weight is applied. The density and thickness of the sponge should be selected to keep the challenge fluid under the base end of the rod long enough for the weight bearing rod to create a hydrostatic pressure between the fluid and the test material. The ideal sponge will not allow any movement of fluid away from the rod base end. In one embodiment, a latex foam sponge 0.135 inch thick made by Shearing-Plough for foot and shoe padding is used. Foam sponge selection depends upon the surface tension and viscosity of the challenge liquid. Liquids which have high surface tensions and viscosities move slower and, therefore, require lower density foam sponge.

Figure 4:
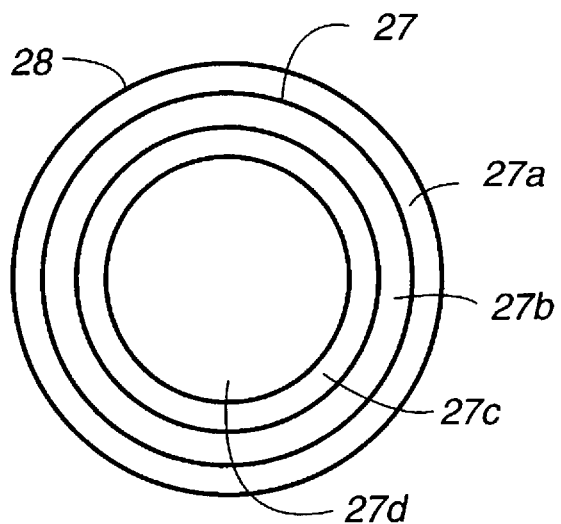
FIG. 4 is an end view of yet another alternate embodiment of the rod used in FIG. 1.

To increase this hydrostatic effect, the embodiment shown in FIG. 4 might be used wherein the rod base 27 has concentric circles of varying widths cut at different depths and at different distances apart with the inner most concentricity having the greatest depth. All of the concentric circles combined, however, do not equal the combined thickness of the sponge, test material, and paper. The effect of these concentric circles is to force the liquid toward the center which has the lowest pressure until the final peak pressure is applied by the weight bearing rod.

Figure 5:
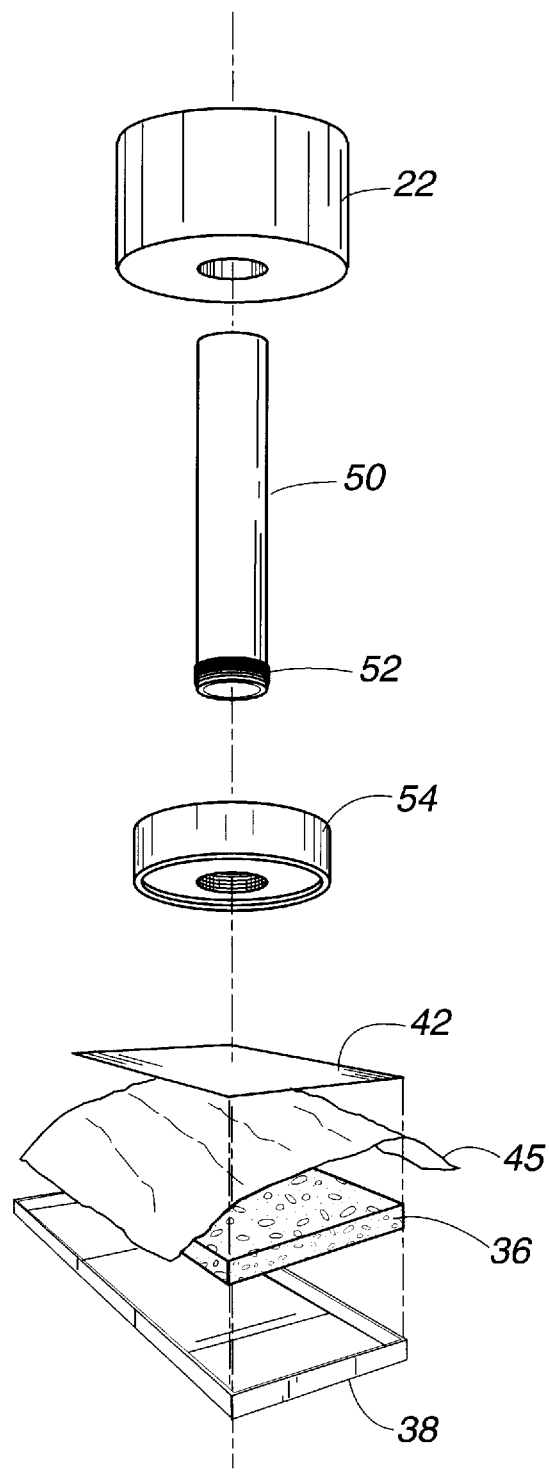
FIG. 5 is an exploded view of an alternate embodiment of a universal penetration test apparatus.
Figure 6:
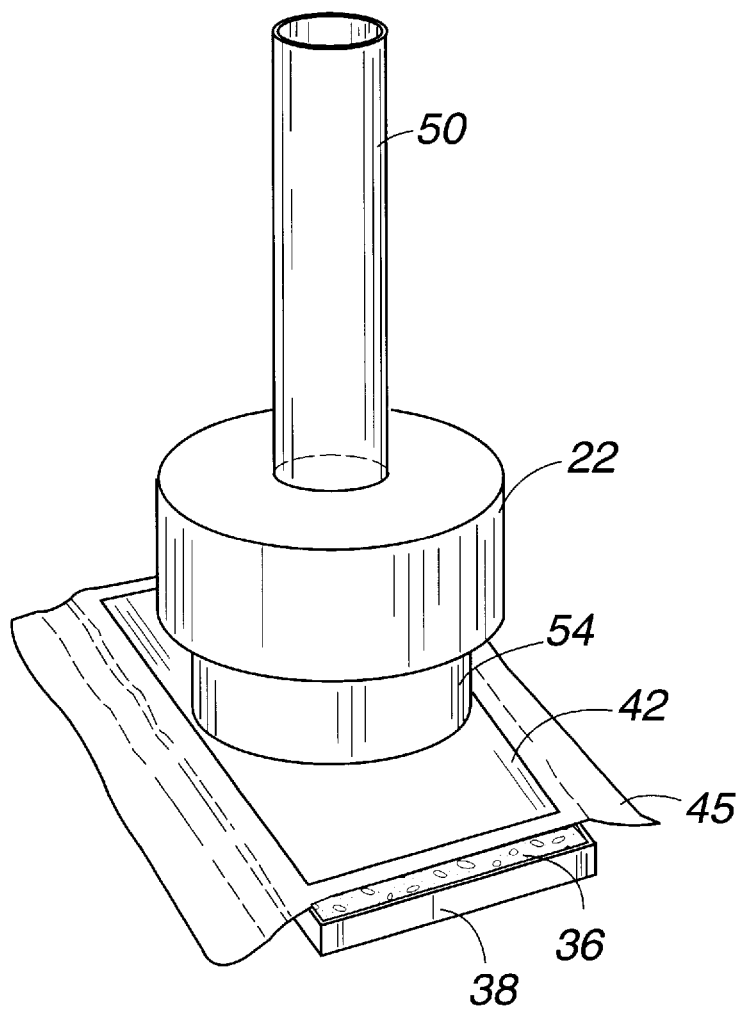
FIG. 6 is a view of the universal penetration test apparatus shown in FIG. 5, in its testing position.

In yet another embodiment of the present invention, as shown in FIGS. 5 and 6, a rod 50 might be used with a threaded end 52 which screws into a base 54 which serves as both the contact surface against the test material 45 and as the support for the weights 22 which slide down over the rod 50 and rest against the upper surface of the base, thereby eliminating the need for the sleeve and the supporting frame assembly 32. The base of the rod 50 in this embodiment can also include the concentric ring feature.

Figure 7:
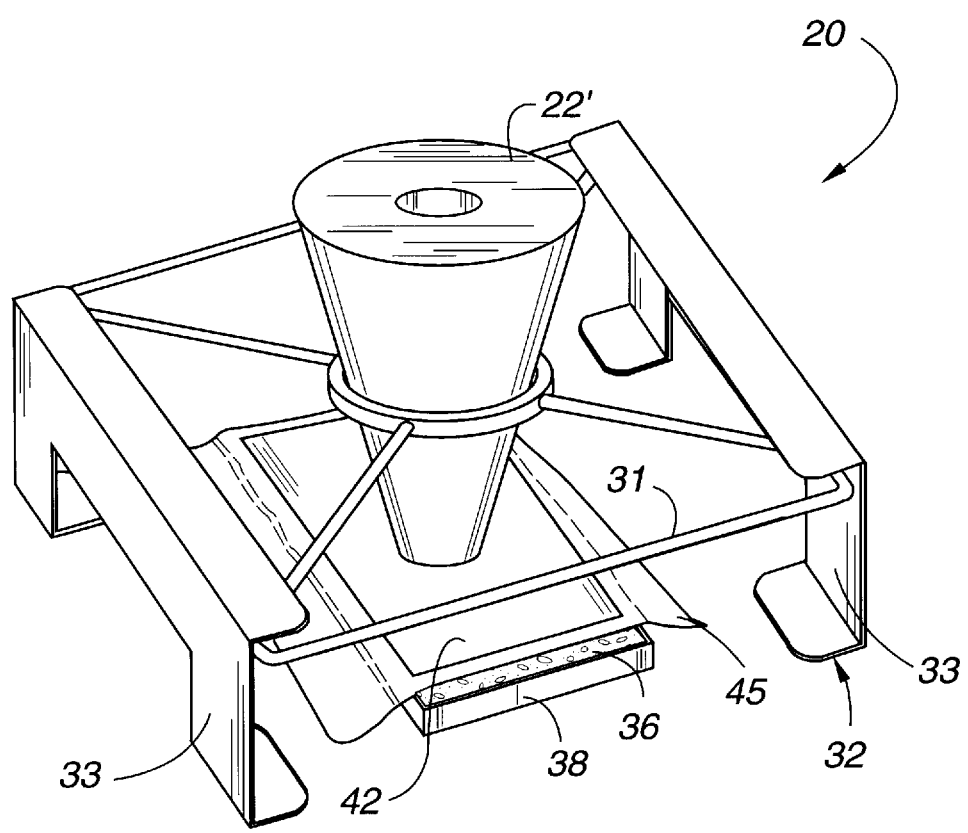
FIG. 7 is a perspective view of an alternate embodiment of the universal penetration test apparatus.

Yet another embodiment of the present invention, as shown in FIG. 7, comprises conical weights 22' of different sizes with the top and bottom of each weight capable of serving as a contact surface against the test material 45, thereby eliminating the sleeve, and the rod, and allowing for greater variations in applied pressures, simply by switching the weight end-for-end. However, this embodiment prevents viewing the test in progress. The weights must be removed to check the penetration. This embodiment can also include the concentric ring features.

Yet another embodiment of the present invention includes the use of spherical weights of different sizes. This embodiment eliminates the need for the rod, shaft, and stand, but prevents viewing the test in progress. The weights must be removed to see if the test material has been penetrated.

Ideally the components of the tester device are sterilizable by conventional means such as gas or chemicals.

Figure 8:
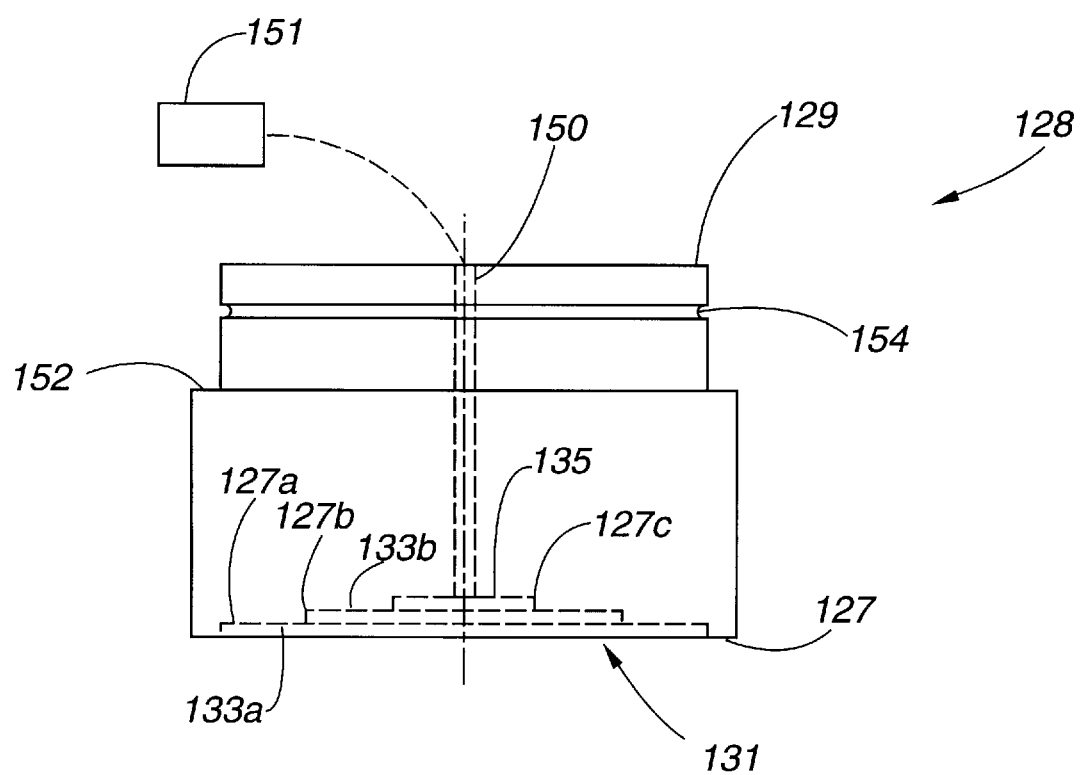
FIG. 8 illustrates side view of an alternative embodiment of a rod which may be employed by the universal penetration test apparatus of the present invention.
Figure 9:
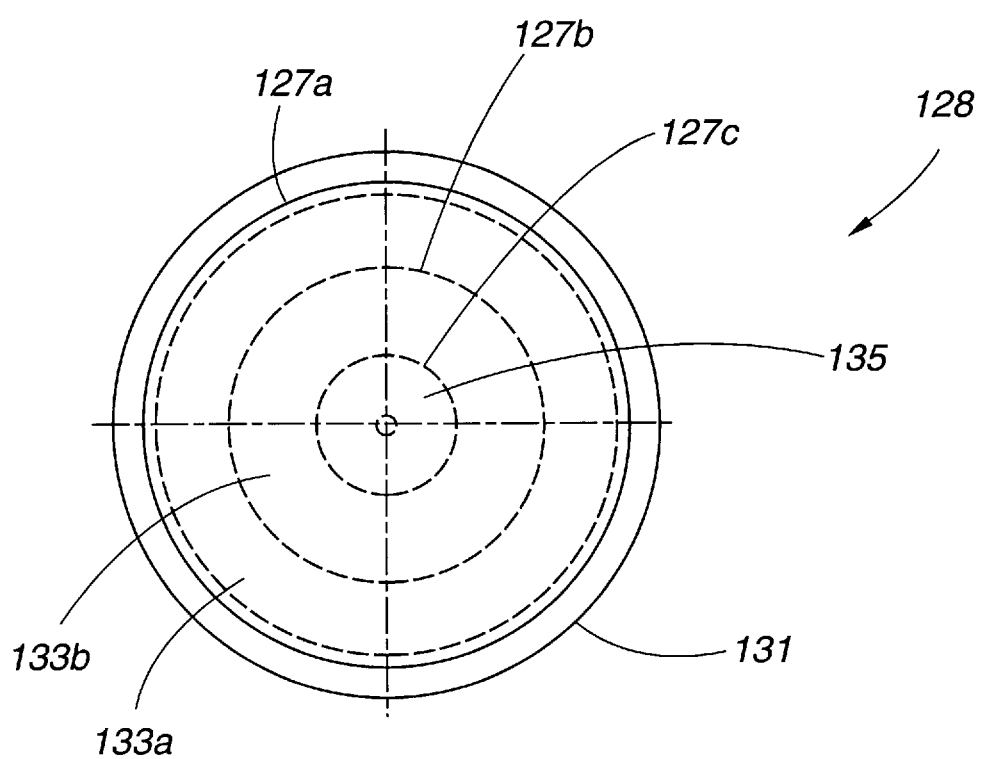
FIG. 9 shows a plan view of the pressure head of the rod of FIG. 8.

FIGS. 8 and 9 show an alternative rod 128 for use with a universal material penetration test apparatus of the present invention. The rod 128 has a top end 129 and a base end 127 which functions as a pressure head 131. The base end 127 of the rod 128 has a plurality of concentric circles 127a–c, of varying widths, cut at different depths and at different distances apart, with the innermost concentric circle or center of the rod having the greatest depth. Concentric circles 127 a–c form stepped annular rings 133 a–b and the concentric circle 127c defines a recessed circle 135 concentric about the center of the base end 127 of the rod 128 and stepped down from the annular ring 133b.

The rod 128 has a central passageway 150 which extends longitudinally throughout the length of the rod 128. The central passageway 150 is preferably in fluid (liquid or gas) communication with the innermost concentricity and prevents air or liquid back pressure from developing when mechanical pressure is applied to the base end 127 of the rod 128.

An exterior flange 152 circumscribes the exterior of the rod 128 at a location between the base end 127 and the top end 129 of the rod 128. The exterior flange 152 typically abuts against a frame assembly to facilitate mounting the rod 128 within an opening in the frame assembly. The rod 128 also defines a circular O-ring groove 154 located adjacent to the top end 129 of the rod 128. The O-ring groove 154 typically receives an O-ring which further facilitates mounting the rod 128 within an opening in a frame assembly.

In use, the base end 127 of the rod 128 is preferably pressed against the test material 45. As previously described, the test material 45 is pressed between the base end 127 of the rod 128 and the sponge 36 which has been saturated with the challenge fluid. As the base end 127 of the rod 128 is pressed against the test material 45, the central passageway 150 prevents air or liquid back pressure from developing which may interfere with the outcome of the test. The increasing pressure differential generated by the concentric rings 127a–c causes the challenge fluid to flow towards the center of the rod 128. When the challenge fluid reaches the center of the rod 128, the pressure causes the challenge fluid to flow through the test material 45 and up the central passageway 150.

It will be appreciated that a pressure sensor 151 such as a manometer or pressure transducer can be fluidly connected to the central passage way 150, preferably at a location adjacent to the top 129 of the rod 128, to measure the amount of pressure required to cause test material 45 failure. It will also be appreciated that plugging the central passage way 150 will create negative pressure. It will further be appreciated that the absorbent paper 42, which was previously described in the specification, is preferably not employed to separate the base end 127 of the rod 128 from the pad 36 during the testing process.

Figure 10:
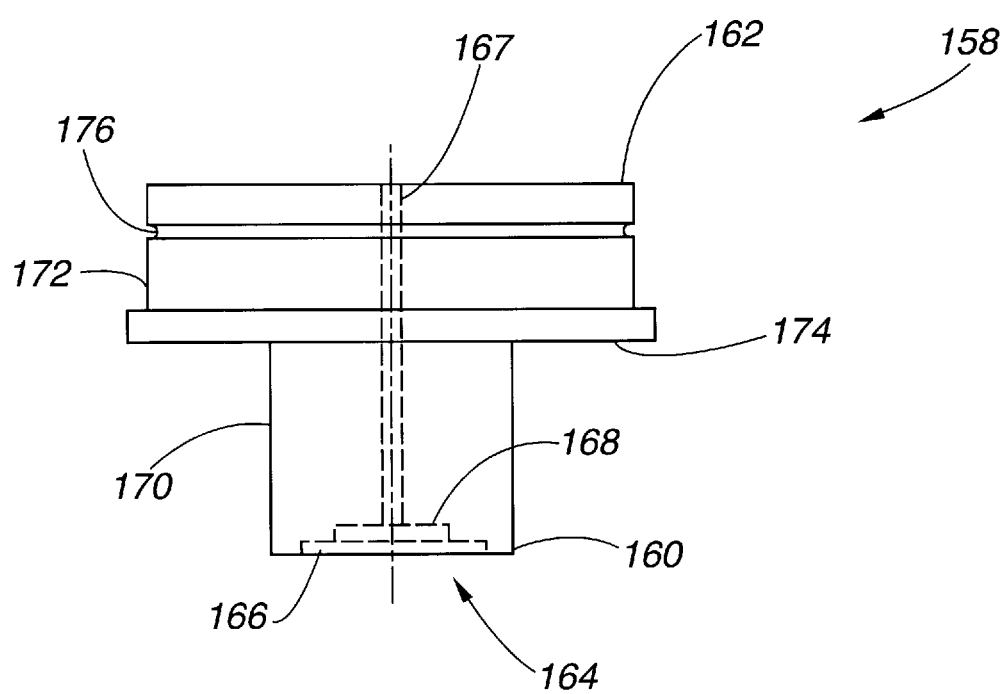
FIG. 10 illustrates a side view of an alternative embodiment of a rod which may be employed by the universal penetration test apparatus of the present invention.
Figure 11:
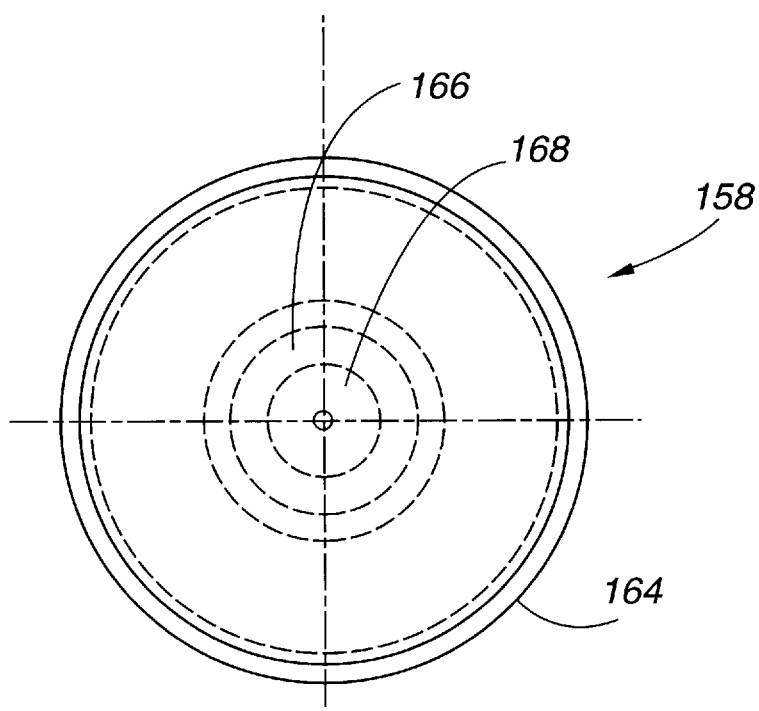
FIG. 11 shows a plan view of the pressure head of the rod of FIG. 10.

FIGS. 10 and 11 show a modified rod 158 having a first end 160 and a second end 162. The first end 160 functions as a pressure head 164 and includes a recessed annular ring 166 and a recessed central circle 168 which is stepped down from the annular ring 166. A longitudinal passageway 167 extends longitudinally through the center of the rod 158 and is in fluid (air or liquid) communication with the recessed central circle 168. The rod 158 includes a first portion 170 adjacent the first end 160 that is integral with a second portion 172 adjacent to the second end 162. The second portion 172 has a diameter substantially larger than the diameter of the first portion 170 such that a circular outer flange 174 is defined. The second portion also defines a circumferential O-ring groove 176 for receiving an O-ring.

Figure 12:
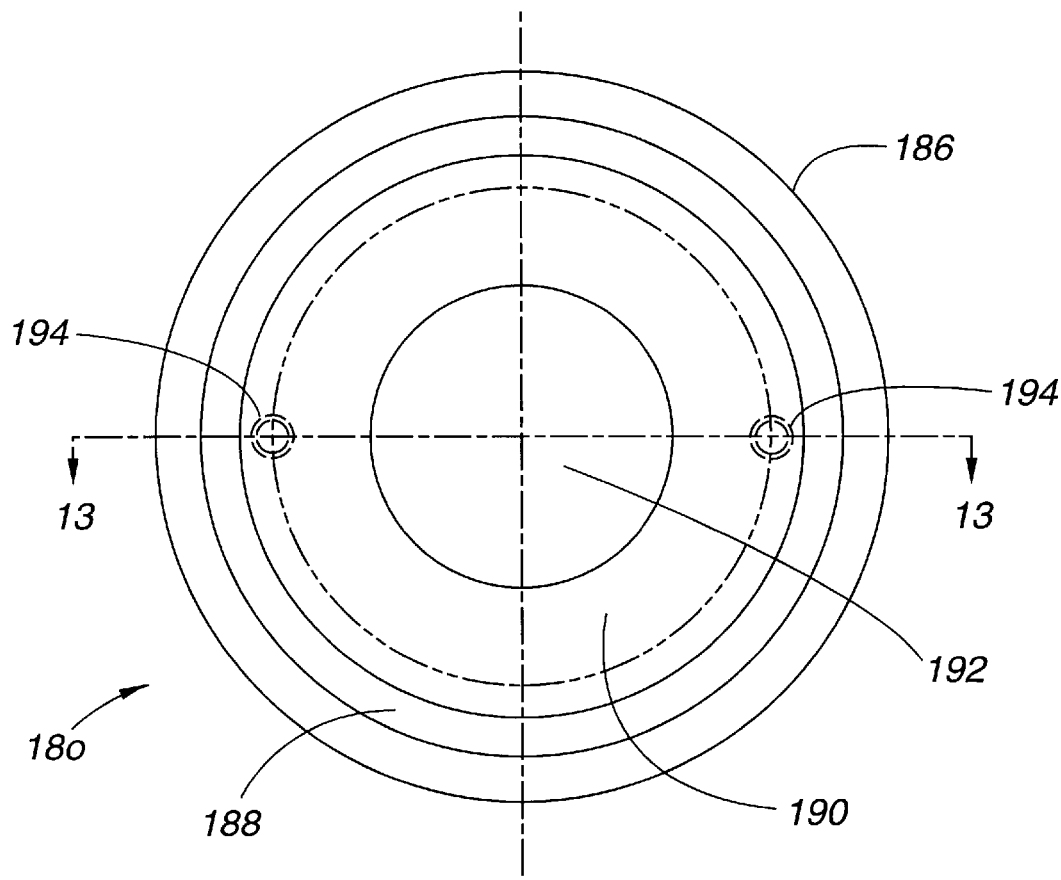
FIG. 12 illustrates a plan view of the pressure head of an alternative embodiment of a rod which may be employed by the universal penetration test apparatus of the present invention.
Figure 13:
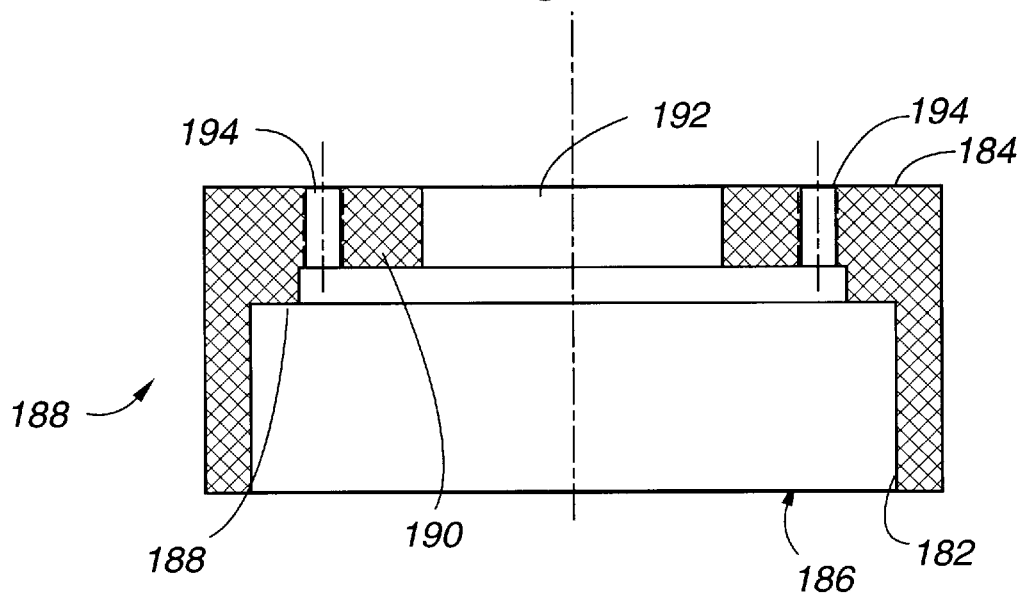
FIG. 13 shows a sectional view of the pressure head of FIG. 12 taken along section line 13—13.

FIGS. 12 and 13 show a modified rod 180 having a first end 182 and a second end 184. The first end 182 functions as a pressure head 186 and includes a first recessed annular ring 188, a second recessed annular ring 190 stepped down from the first annular ring 188, and a recessed central circle 192 which is stepped down from the second annular ring 190. The circles defining the first and second annular rings 188, 190 and the recessed circle 192 are substantially concentric. A pair of longitudinal passageways 194 extend longitudinally through the rod 180 and have openings on opposite sides of the second annular ring 190.

It will be appreciated that the present invention includes pressure heads having different numbers and diameters of concentric circles than those specifically shown. Additionally, the present invention includes pressure heads having different stepping depths than those specifically shown.

It will further be appreciated by those skilled in the art that pressure heads constructed in accordance with the principles of the present invention, either with or without central longitudinal openings, have a variety of uses outside the scope of material testing. For example, the pressure heads may be employed in an internal combustion engine by machining the annular rings and the central recess into the combustion side of an engine piston or head. For such a use, the concentric circles of the pressure heads increase combustion efficiency by directing the combustion pressure to the center of the piston and by creating a more efficient vacuum for the intake of gases. It will also be appreciated by those skilled in the art that the pressure heads may be utilized in pumps to increase the pressure flow rate of liquids. Furthermore, the pressure heads may be employed to increase flow rates in any devices which moves liquids or gases.

It has been determined by the inventor that for use within a universal penetration test apparatus, it is preferred to employ pressure heads having a diameter approximately equal to 2¼ inches. The increased diameter size allows researchers to use a smaller number of samples to achieve the same level of accuracy in study results. For example, in normal use a pressure head having a ¼ inch diameter may require 36 samples to achieve accurate study results. In contrast, a 2¼ inch pressure head has been determined to only require 6 samples to achieve the same level of accuracy. Therefore, by employing a 2¼ inch diameter pressure head, the required testing time is greatly reduced.

Although a 2¼ inch diameter pressure head is preferred for use in a universal penetration test apparatus, it will be appreciated that the present invention includes pressure heads having various sizes.

Figure 14:
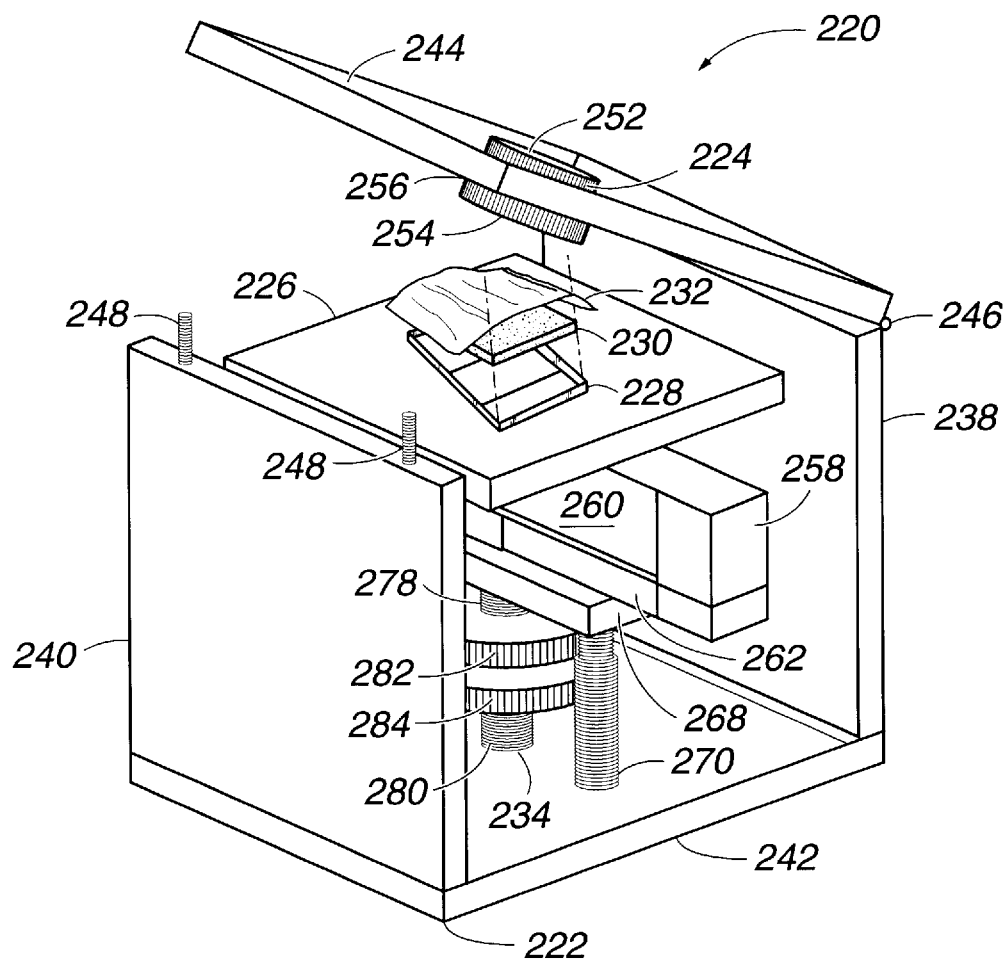
FIG. 14 shows a perspective view of an alternative universal penetration test apparatus constructed in accordance with the principles of the present invention, the apparatus is shown with the top open.
Figure 15:
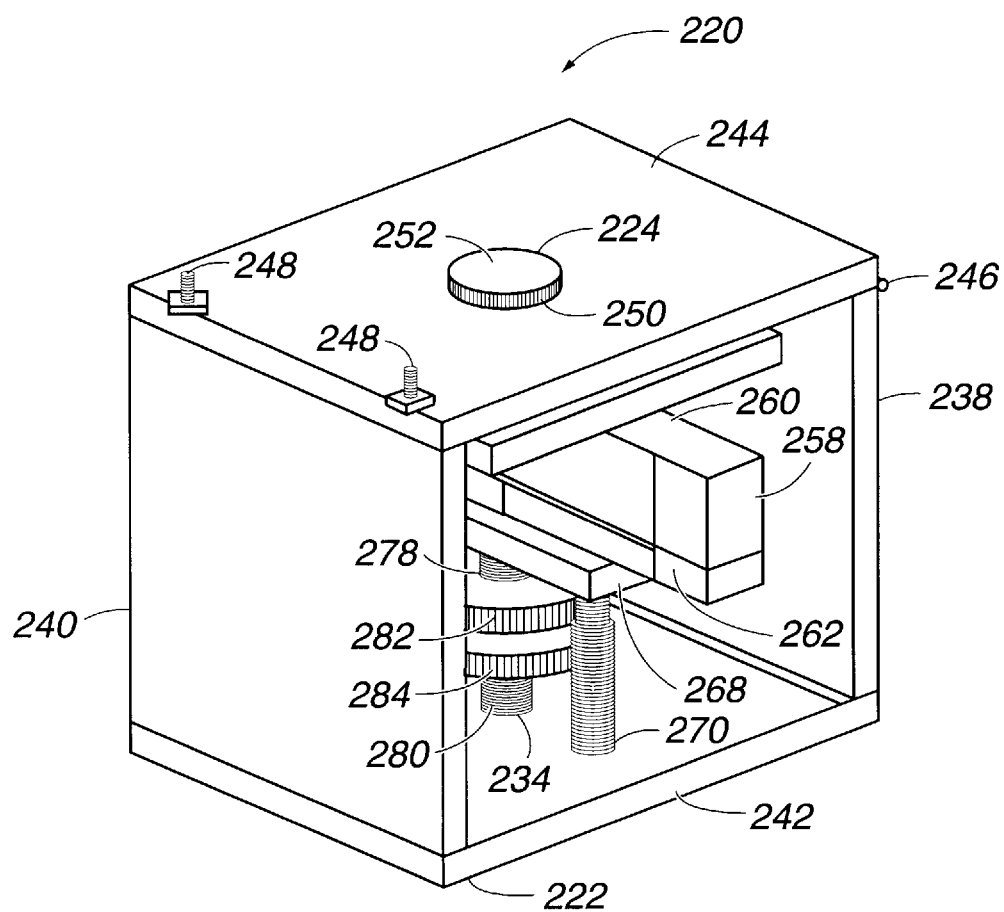
FIG. 15 shows the universal penetration test apparatus of FIG. 14 with the top closed.
Figure 16:
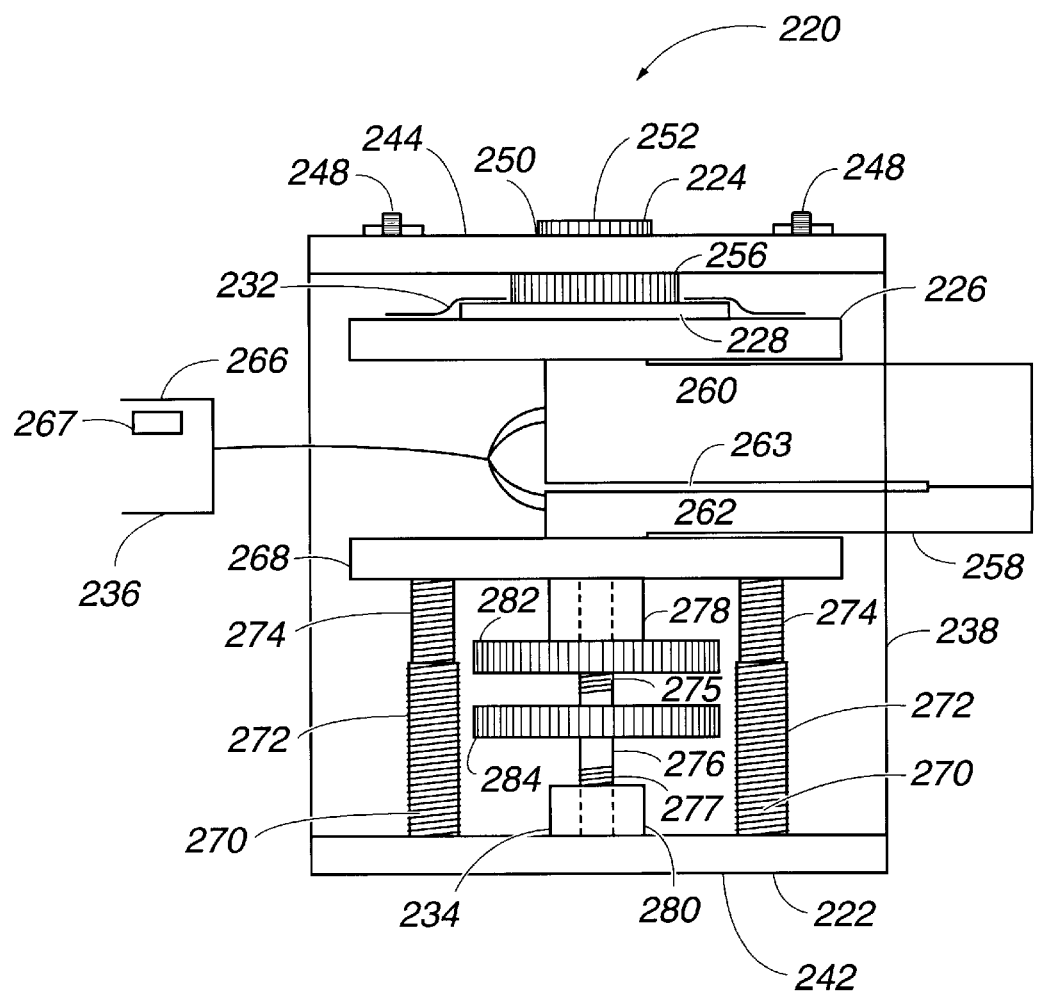
FIG. 16 shows a side view of the universal penetration test apparatus of FIG. 14 with the side removed to illustrate the internal assembly of the apparatus.

It will be appreciated that the present invention is not limited to universal material test devices which employ compression assemblies having weights to generate compressive loading on a test material. For example, FIGS. 14–16 illustrate a universal material penetration test apparatus 220 which is another representative embodiment of the present invention. Generally, the universal material tester 220 includes a support frame 222 which supports a rod 224. The rod 224 is positionable above a support platform 226 which supports a tray 228 containing a pad 230 which typically is saturated with a challenge fluid. The test material 232 is preferably positioned between the rod 224 and the pad 230. A compression assembly such as a screw assembly 234 preferably moves the support platform 226 vertically such that the test material 232 is compressed between the rod 224 and the pad 230. The universal material penetration test apparatus 220 also preferably includes a weighing indicator assembly 236 for measuring the mechanical pressure exerted on the test material 232.

The support frame 222 of the universal penetration test apparatus 220 is generally square or rectangular and includes a first and second side plate 238 and 240 extending between a bottom plate 242 and a top plate 244. The plates 238, 240, 242, and 244 are preferably constructed of aluminum, plastic or a comparable material. The top plate 244 is pivotally connected to the side plate 238 by a pair of hinges 246. A pair of conventional latch pins 248 extend upward from the top of side plate 240. When the top plate 244 is pivoted down against the second side plate 240, the latch pins 248 pass through latch pin holes in the top plate 244. By threading conventional nuts on the latch pins 248 when the top plate 244 is pivoted down against the second side plate 240, the top plate 244 is held rigidly in the closed position as shown in FIG. 15. When the nuts are removed from the latch pins 248, the top plate 244 can be moved pivotally upwards to an open position as shown in FIG. 14. The top plate 244 also defines a generally circular rod opening 250 for receiving the rod 224 and securing the rod to the support frame 222.

The bottom plate 242 is preferably rigidly connected to both the first side plate 238 and the second side plate 240.

The rod 224 of the universal penetration test apparatus 220 is preferably generally cylindrical and is preferably constructed of a clear material such as plexiglass. The rod 224 has a top end 252 and a base end 254. The rod 224 also includes a circumferential flange portion 256 located adjacent to the base end 254 of the rod 224.

It will be appreciated that the base end 254 of the rod 224 functions as a pressure head. The base end 254 may have a variety of configurations. For example, the base end 254 may be flat or may have a plurality of concentric circles having different depths as previously described in the specification. Additionally, as also described previously in the specification, the rod 224 may have a central passageway extending longitudinally therethrough for preventing the build-up of back pressure at the pressure head of the rod 224.

The rod 224 is inserted in the rod opening 250 of the top plate 244 such that the flange portion 256 abuts against the bottom surface of the top plate 244 and the top end 252 of the rod is located slightly above the top surface of the top plate 244. The rod 224 may be equipped with an O-ring around its diameter for engaging the inner surface of the rod opening 250 in order to retain the rod 224 within the rod opening 250. When the top plate 244 is moved to the close position as shown in FIG. 15, the base end 254 of the rod 224 is located directly above and slightly displaced from the test material 232.

As previously described in the specification, the test material is preferably spread over the pad 230 such that the material 232 is located between the pad 230 and the rod 224. The pad 230, which is saturated with the challenge fluid, is preferably held within the tray 228 which rests upon the support platform 226.

The support platform 226 of the universal penetration tester 220 is preferably made of a metal such as aluminum and is preferably supported by a load cell 258 which is connected to the bottom of the support platform 226.

The load cell 258 forms a part of the weighing indicator assembly 236 and operates generally like a "wheatstone bridge." The load cell 258 preferably has 4 strain gauges which represent the resistive elements of the wheatstone bridge. The strain gauges measure stress and strain within the load cell 258 as the load cell 258 is subjected to a load. A preferable load cell is sold by Rice Lake Weighing Systems and has Model No. PL1040-10CHIG. The load capacity of the load cell 258 preferably ranges from 220–250 pounds.

As shown in FIG. 16, the load cell 258 has an upper portion 260 and a lower portion 262 which are separated by a gap 263. Wires 264 electrically connect the strain gauges of the load cell 258 to a data processor which functions as a weighing indicator 266. A preferred weighing indicator is sold by A & D Weighing and has Model No. AD-4322AMKII.

When the load cell 258 is compressed, the upper portion 260 and the lower portion 262 are forced together such that the gap 263 is narrowed. The movement of the upper portion 260 and the lower portion 262 generates strain within the load cell 258 which is measured by the strain gauges. The strain gauges generate electrical current which flows through the wires 264 from the load cell 258 to the weighing indicator 266. The weighing indicator 266 measures the amount of current flowing through the wires 264 and converts the current measurement data to pressure data which is representative of the compressive forces exerted on the load cell 258. The weighing indicator 266 preferably displays the pressure data on a digital monitor 267. The pressure data may be displayed in a variety of units.

As shown in FIG. 16, the lower portion 262 of the load cell 258 is supported on a load cell platform 268 which is connected to the base of the load cell 258. Similar to the support platform 226, the load cell platform 268 is preferably constructed of aluminum or a like material.

A pair of substantially vertical support cylinders 270 connect the load cell platform 268 to the bottom plate 242 of the support frame 222. Each of the support cylinders includes an outer cylinder 272 having a longitudinal inner bore for slidingly receiving an inner support member 274. The bases of the outer cylinders 272 are rigidly connected to the top of the bottom plate 242 while the tops of the inner support members 274 are connected to the load cell platform 268. Because the inner support members 274 slidingly engage the outer cylinders 272, the support cylinders 270 allow for the vertical movement of the load cell platform 268.

The screw assembly 234 of the universal material penetration tester 220 is located below the load cell platform 268. The screw assembly 234 includes a substantially vertical differential screw 276 which generally extends between the bottom of the load cell platform 268 and the top of the bottom plate 242. The differential screw 276 has an upper portion having first male right hand screw threads 275 and a lower portion having second male right hand screw threads 277. The first threads 275 have a slightly greater pitch than the second threads 277.

The screw assembly 234 also includes a cylindrical top member 278 rigidly connected to the bottom of the load cell platform 268 and a cylindrical bottom member 280 rigidly connected to the bottom plate 242 of the support frame 222. The top portion of the differential screw 276 is inserted within a non-threaded clearance bore defined by the cylindrical top member 278. The bottom portion of the differential screw 276 is inserted within a threaded bore defined by the cylindrical bottom member 280. The threaded bore of the bottom member 280 has female right hand screw threads which mate with the male second threads 277 such that the bottom portion of the differential screw 276 is threaded into the bore of the bottom member 280.

A first turning wheel 282, such as a thumb screw, is mounted on the top portion of the differential screw 276. The first turning wheel 282 has a central bore having female right hand screw threads which mate with the male first threads 277 of the differential screw 276. Additionally, a second turning wheel 284 is rigidly mounted on the differential screw 276 below the first turning wheel 282.

When the first turning wheel 282 is rotated in a first direction (right hand direction relative to the threads 275), the first turning wheel 282 climbs upward along the first threads 275 of the differential screw 276 until it contacts the top member 278. Once the first turning wheel 282 contacts the top member 278, the continued rotation of the first turning wheel 282 in the first direction forces the top member 278 and the load cell platform 268 vertically upward along the differential screw 276. As the load cell platform 268 moves upward, it pushes the load cell 258 and the support platform 226 upward until the test material engages the base end 254 of the rod 224.

The continued rotation of the first turning wheel 282 in the first direction compresses the test material 232 between the base end 254 of the rod 224 and the pad 230 and also compresses the load cell 258 between the support platform 226 and the load cell platform 258. As the load cell 258 is compressed and strained, it generates electric current which flows through the wires 264 to the weighing indicator 266. The weighing indicator 266 converts the current data into pressure data which is representative of the magnitude of mechanical pressure exerted by the base end 254 of the rod 224 on the test material 232. The pressure data is displayed by the digital monitor 267 of the weighing indicator 266 such that an operator of the universal material penetration test apparatus 220 will know the exact pressure which is being exerted upon the test material 232.

When the pressure exerted on the test material 232 is slightly below the desired pressure, the operator stops rotating the first turning wheel 282 and begins to rotate the second turning wheel 284 in a second direction. By rotating the second turning wheel 284 in the second direction, the second threads 277 on the lower portion of the screw 276 are moved in a right hand direction relative to the threads in the bore of the bottom member 280 causing the differential screw 276 to work its way downward along the threads in the bore of the bottom member 280. Simultaneously, the differential screw 276 is rotated in a left hand direction relative to the threads defined by the first turning wheel 282 causing the first turning wheel 282 to climb upward along the first threads 275 of the differential screw 276 thereby further pushing the first top member 278 upward along the differential screw 276.

Because the first threads 275 of the differential screw 276 have a slightly steeper pitch than the second threads 277, the net effect of the downward movement of the differential screw 276 relative to the bottom member 280 and the upward movement of the top member 278 relative to the differential screw 276 is a slight upward movement of the top member 278. As the top member 278 is moved slightly upward by the rotation of the second turning wheel 284, the test material 232 is slightly further compressed between the base end 254 of the rod 224 and the pad 230 and the load cell 258 is slightly further compressed between the support platform 226 and the load cell platform 268. Because the rotation of the second turning wheel 284 results in only slight pressure variations, the operator can easily and precisely adjust the pressure to the desired level. Essentially, the first turning wheel 282 operates as a course adjustment and the second turning wheel 284 operates as a fine adjustment.

When the test is complete, the first turning wheel is rotated in the second direction such that the load cell platform is moved vertically downward and the test material 232 is moved vertically away from the bottom end 254 of the rod 224. Also, the second turning wheel 284 is preferably rotated in the first direction to center the turning wheel 284 and to reset the apparatus for the next test.

In operation, the top plate 244 of the universal material penetration tester 220 is first pivoted to the open position as shown in FIG. 14. Once the top plate 244 is open, the rod 224 is inserted in the rod opening 250 of the top plate 244 and the tray 228 is placed on the center of the support platform 226. As described previously, the tray 228 contains the pad 230 which is saturated with the challenge fluid. The test material 232 is placed over the pad 230 and the top plate 244 is pivoted to the closed position and nuts are screwed on the latch pins 248 such that the top plate 244 is not free to open. At this point in the testing process, the base end 254 of the rod 224 is located directly above the test material 232.

Once the top plate 244 of the support frame 222 is closed and secured, the first turning wheel 282 (course adjustment) is rotated in the first direction such that the support platform 226 moves vertically upward causing the test material 232 to be compressed against the base end 254 of the rod 224. As the operator turns the first turning wheel, the pressure exerted on the test material 232 by the rod 224 is digitally displayed by the weighing indicator 266. When the pressure on the test material 232 approaches the desired level, the operator preferably stops rotating the first turning wheel 282 and begins rotating the second turning wheel 284 in the second direction. The second turning wheel 284 (fine adjustment) allows the operator to precisely control the pressure exerted by the rod 224 on the test material 232.

As the pressure exerted by the rod 224 against the test material 232 increases, the operator can watch the effect of the pressure variation on the specimen by looking through the top of the transparent rod 224 which is locked into the top plate 244.

After the test is complete, the first turning wheel 282 is rotated in a second direction such that the support platform 226 is moved away from the base end 254 of the rod 224. When the test material is no longer in contact with the base end of the rod 224, the nuts are removed from the latch pins 248 and top plate 244 is opened such that the universal material penetration test apparatus 220 can be prepared for another test.

Figure 17:
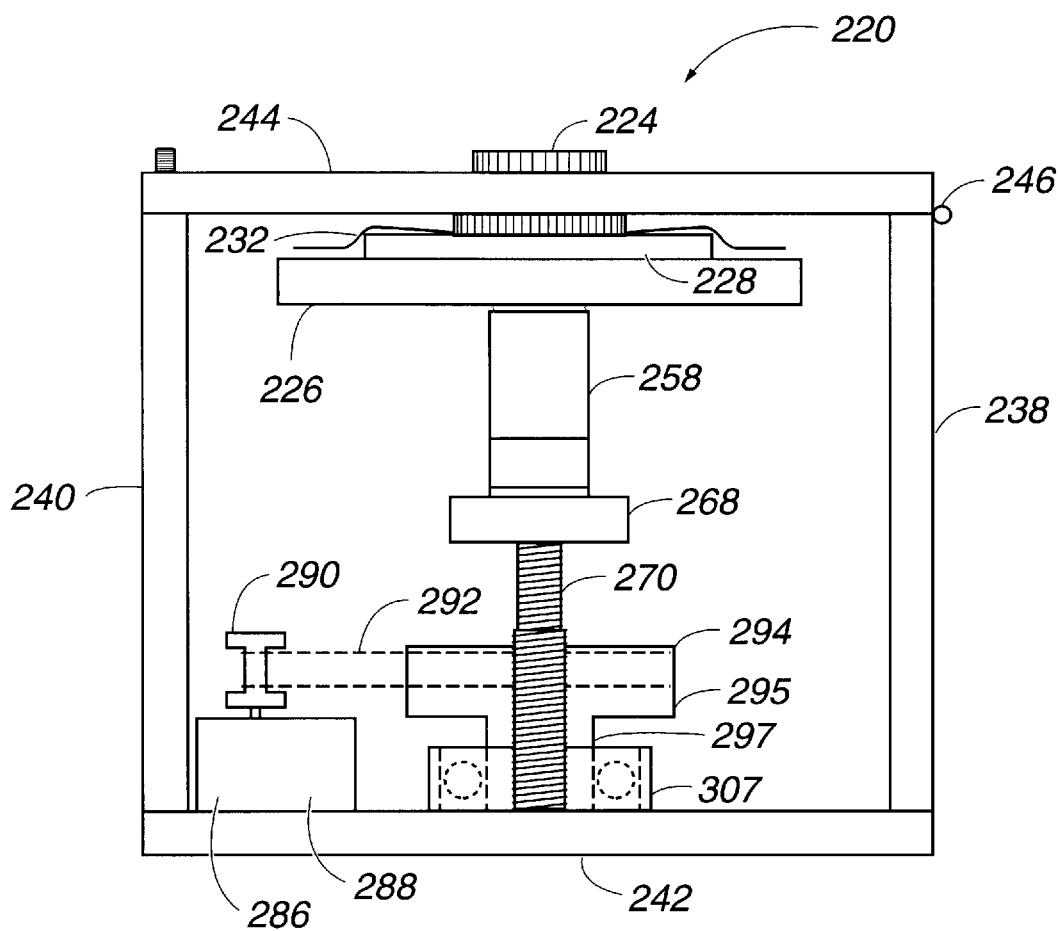
FIG. 17 shows a side view of an alternative universal penetration test apparatus constructed in accordance with the principles of the present invention.

FIG. 17 shows a modified universal material penetration test apparatus 220' having the same construction as the universal material test apparatus 220 except that the screw assembly 234 has been replaced with a motorized screw assembly 286, which operates like a screw jack, for raising and lowering the support platform 226.

The motorized screw assembly 286 includes a conventional electric motor 288. The electric motor 288 has a timing belt pulley 290 which is connected by a timing belt 292 to a driven sprocket 294 or turning wheel. The driven sprocket 294 has a disk shaped geared portion 295 for interfacing with the belt 292 and a central hub portion 297 extending outward from the geared portion 295. A cylindrical opening 301 extends through the centers of the hub and geared portions 297, 295.

Figure 18:
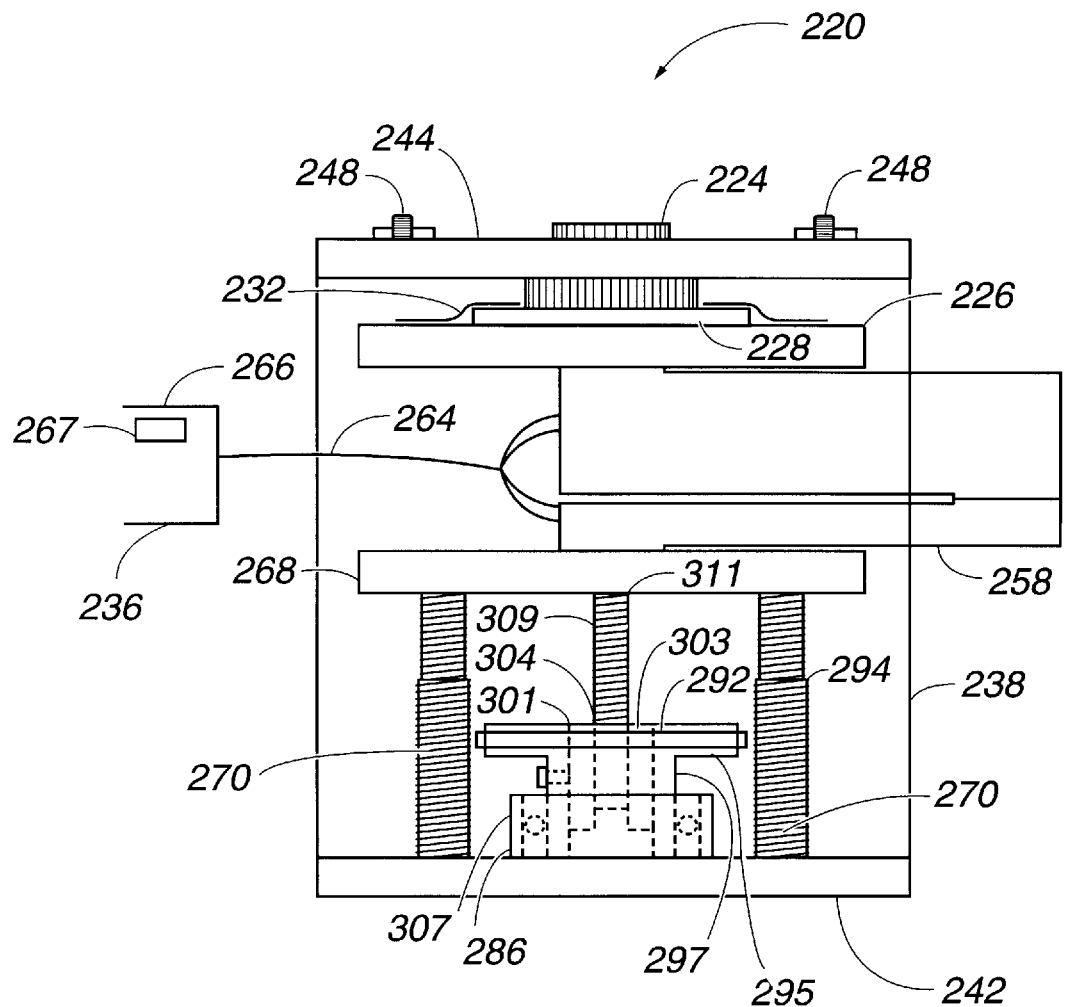
FIG. 18 shows another side view of the apparatus of FIG. 17.

With reference to FIG. 18, a hollow cylindrical drive nut 303 is inserted within the cylindrical opening 301 of the driven sprocket 294. The drive nut 303 is fixedly connected to the driven sprocket 294 by a set screw passing through the hub portion 297 of the driven sprocket 294 and engaging the drive nut 303. The drive nut 303 has an inner hole 304 and includes female threads located within the hole 304.

Still with reference to FIG. 18, the motorized screw assembly 286 also includes a bearing 307 rigidly mounted to the bottom plate 242 of the support frame 222. The hub portion 297 of the driven sprocket 294 rests upon the inner race of the bearing 307 such that the bearing 307 facilitates rotation of the driven sprocket 294 by the motor 288. A substantially vertical screw 309 extends through the inner hole 304 of the drive nut 303. The screw 309 has a top end 311 which is non-rotatedly connected to the bottom of the load cell platform 268. The screw 309 has male threads which mate with the female threads of the drive nut 303 such that when the driven sprocket 294 is rotated in a first direction, the screw 309 is pushed vertically upward by the interaction of the threads. Similarly, when the driven sprocket 294 is rotated in a second direction, the screw 309 is pulled vertically downward by the interaction of the threads.

Referring again to FIG. 18, because the top of the screw 309 is connected to the bottom of the load cell platform 268, when the screw 309 is driven upward by the rotation of the driven sprocket 294 in the first direction, the load cell platform 268 simultaneously moves upward causing the test material 232 to be compressed between the rod 224 and the pad 230. Similarly, when the screw 309 is driven downward by the rotation of the driven sprocket 294 in the second direction, the test material 232 moves vertically away from the rod 224.

Referring to FIGS. 17 and 18, the drive motor 288 preferably includes an up/down switch for selectively driving the driven sprocket 294 in the first and second directions. An operator of the universal material penetration test apparatus 220' can precisely control the pressure on the test material 232 by turning the motor switch to the up position such that the electric motor 288 drives the drive sprocket 294 in the first direction. The operator watches the digital pressure readout displayed by the weighing indicator 266 and turns off the power to the electric motor 288 when the desired pressure is reached. After the test is complete, the electric motor switch is moved to the down position causing the electric motor 288 to drive the driven sprocket 294 in the second direction causing the test material 232 to move vertically away from the rod 224.

Still with reference to FIGS. 17 and 18, it will be appreciated that the motor 288 may be electrically connected and controlled by the weighing indicator 266. For such a configuration, the desired level of compression is entered into the weighing indicator 266 and the weighing indicator 266 electronically controls the motor 288 such that the desired pressure is attained.

It will be appreciated that the universal material penetration tester of the present invention includes other screw drive assembly configurations which could be adapted by those skilled in the art to vertically move the load cell platform 268 such that the test material 232 is compressed by the rod 224. Additionally, it will be appreciated that the load cell platform 268 may be vertically moved by other compression assemblies such as pneumatic or hydraulic drive cylinders or other drive mechanisms for vertically moving the load cell platform 268.

Figure 19:
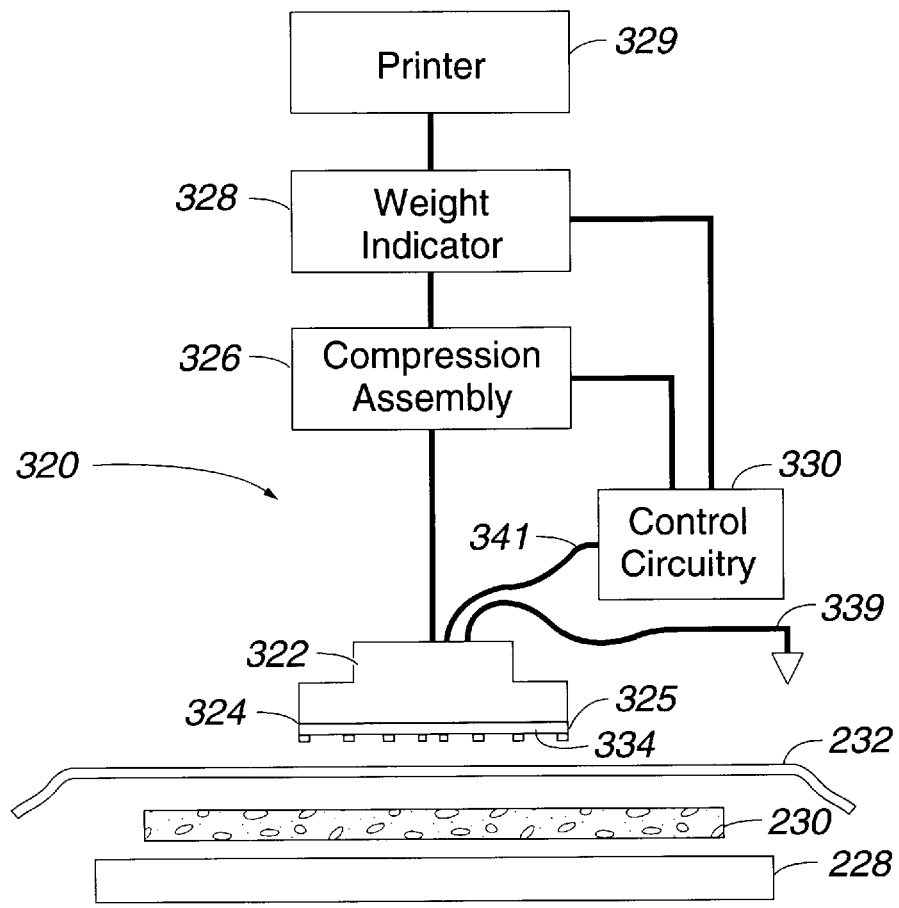
FIG. 19 shows a block diagram of a universal penetration test apparatus having a sensor for detecting when fluid penetrates a test material.

FIG. 19 shows a block/schematic diagram of another penetration test apparatus 320 constructed in accordance with the principles of the present invention. Similar to the aforementioned test apparatuses, the test apparatus 320 includes a container or tray 228 for holding a challenge fluid, and an absorbent pad 230 configured to fit within the tray 228 and absorb the challenge fluid. As previously described with respect to the other illustrated embodiments of the present invention, a test material 232 is compressed against the absorbent pad 230 to test the material's ability to resist penetration of the challenge fluid.

The test apparatus 320 also includes a compression member or rod 322 having a pressure/test head 324 arranged and configured for engaging a top surface of the test material 232. The test material 232 is compressed between the absorbent pad 230 and the test head 324 by a compression assembly 326. A weight indicator 328 is provided with the compression assembly 326 for measuring and displaying the pressure exerted by the test head 324 on the test material 232. The weight indicator 328 includes or is connected to a printer 329 for printing out pressure information.

With respect to FIG. 19, it will be appreciated that an exemplary compression assembly is the motorized screw drive assembly 286 that is illustrated in FIG. 18 and an exemplary weight indicator is the weighing indicator assembly 236 illustrated in FIGS. 16 and 18.

The test head 324 is preferably equipped with a sensing mechanism 325 for automatically detecting when the challenge fluid initially penetrates the test material 232. The sensing mechanism 325 is electrically connected to conventional control circuitry 330 via a positive lead wire 341. A negative lead wire 339 preferably grounds the sensing mechanism. The control circuitry 330 is electrically connected to the compression assembly 326 and the weight indicator 328 to provide an electrical interface between the sensing mechanism 325, the compression assembly 326 and the weight indicator 328. When fluid penetration is detected by the sensing mechanism 325, the control circuitry 330 concurrently deactivates the compression assembly 326 such that no additional pressure is applied to the test material 232 and signals the weight indicator 328 to display and print out the mechanical pressure at which the challenge fluid penetrated the test material 232.

Figure 20:
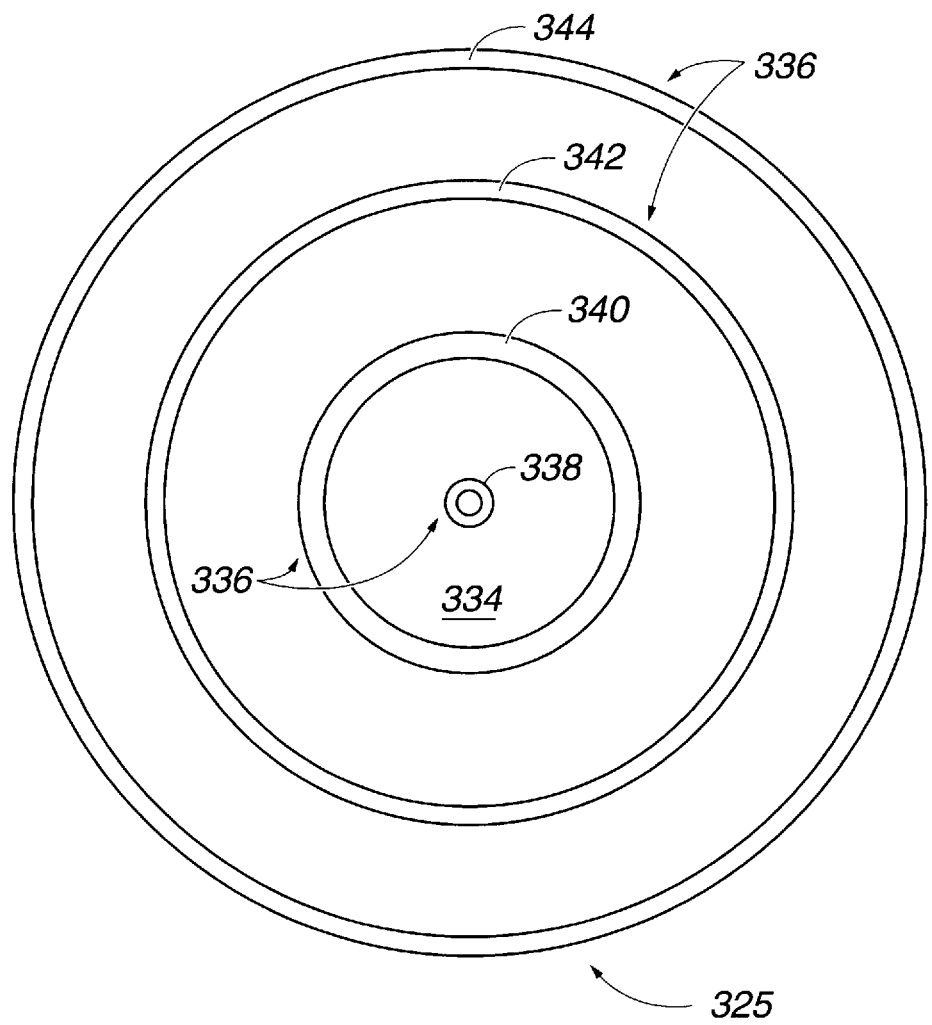
FIG. 20 shows a bottom view of an exemplary test head suitable for use with the penetration test apparatus of FIG. 19.
Figure 21:
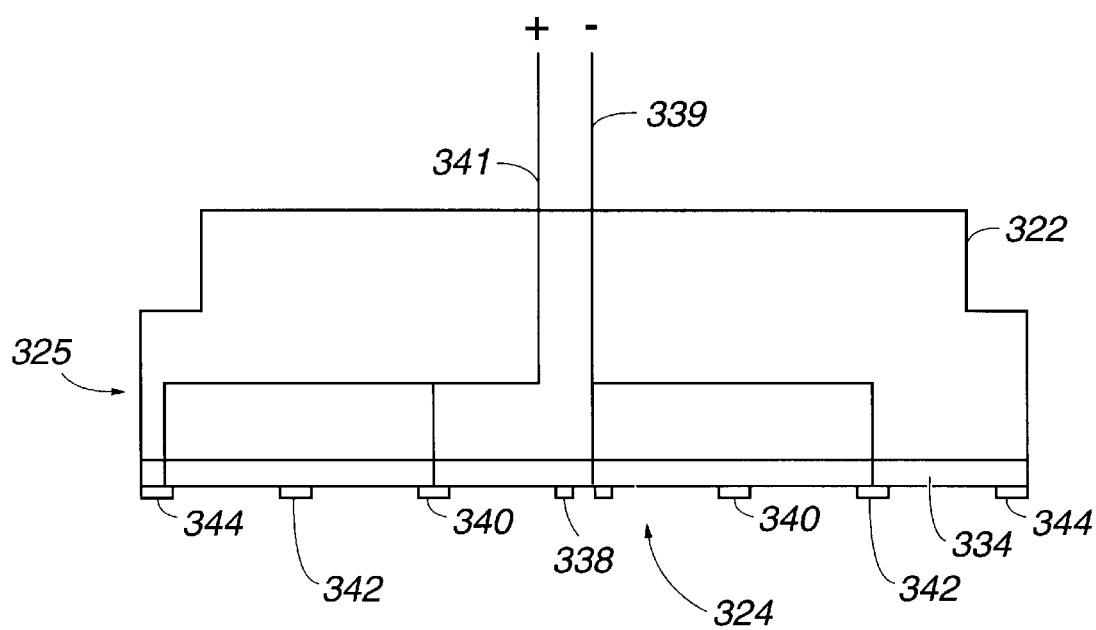
FIG. 21 shows a side view and schematic wiring configuration of the exemplary test head of FIG. 20.

In the embodiment shown in FIGS. 19–21, the sensing mechanism 325 comprises a printed circuit board 334 that is preferably adhesively affixed to the bottom surface of the rod 322 so as to form a face of the test head 324 of the rod 322. To facilitate adhesion of the printed circuit board 334 to the test head 324, it is preferred for the bottom surface of the rod 322 to be substantially flat. A plurality of concentric rings 336 are provided on the surface of the circuit board 334 that faces outward from the rod 322. It will be appreciated that the concentric rings 336 are preferably constructed of highly conductive/low resistant material such as copper, nickel, silver or any other material conventionally used in manufacturing circuit boards. It will be appreciated that the rings 336 can be deposited/fabricated/embossed on the circuit board 334 by a variety of conventionally known techniques. For example, a common manufacturing technique would involve a masking technique such as photolithographic masking.

As shown in FIGS. 19–21, the concentric rings 336 include a interior centrally located first ring 338 (or alternatively a circular conductive pad) concentrically surrounded by second, third and fourth rings 340, 342 and 344 each having a progressively larger diameter. It is preferred for the minimum distance between consecutive concentric rings to be 0.0001 mm. It is also preferred for the minimum thickness and width of the metal that forms the rings to be 0.0001 mm. For example, in one preferred embodiment of the circular sensor head with concentric rings, seventy-six nickel plated copper rings can be used on a 2.25" diameter circular fiber glass substrate, all of which together comprise a circuit board having a surface area of almost 4". Each of the circular, continuous rings has a width of 0.0010", a thickness of 0.0010", and a distance from the next ring of 0.0005". Each ring is alternatively connected to one of the two innermost rings which serve as positive and negative contacts onto which are soldered positive and negative lead wires. The circuit board is glued to a clear plastic test head having the same diameter. The plastic test head has a 0.5 mm center hole for the lead wires to pass through for integration of the sensor circuitry with that of the universal penetration device.

It is preferred for the concentric rings 336 to be alternately connected between a positive and negative voltage. For example, FIG. 21 schematically shows the first and third rings 338 and 342 are electrically connected to the negative voltage lead 339 (which is preferably grounded) while the second and fourth rings 340 and 344 are electrically connected to a positive voltage lead 341. Under normal operating conditions, open circuits exist between the first and second rings 338 and 340, between the second and third rings 340 and 342, and between the third and fourth rings 342 and 344. When each of the circuits are open, no current flows from the positive lead 341 to the negative lead 339. However, when the gap between any two consecutive concentric rings is bridged by a conductive material, such as a conductive challenge fluid, a short circuit occurs and current flows from the positive lead 341 toward the negative lead 339.

The positive lead 341 preferably connects the concentric rings 336 of the test head 324 to the control circuitry 330 while the negative lead 339 is preferably grounded. The control circuitry 330 is constructed and arranged to detect the flow of current between the negative and positive leads 339 and 341. When current is detected by the control circuitry 330, the control circuitry causes the compression assembly 326 to be deactivated and also causes the weight indicator 328 to display and print out the pressure being applied to the test material 232.

In operation of the test apparatus 320, the test material 232 is placed over the absorbent pad 230 that is saturated with the challenge fluid. The compression assembly 326 is then actuated causing the test head 324 to press against the top surface of the test material. The pressure applied by the test head 324 progressively increases until the challenge fluid penetrates the test material 232. When the fluid penetrates the test material 232, a short circuit occurs between two or more of the concentric rings 336 thereby allowing current to flow from the positive lead 341 to the negative lead 339. The current flow is detected by the control circuitry 330 which causes the compression assembly 326 to be deactivated so that no additional pressure is applied to the test material 232. The control circuitry 330 also concurrently causes the weight indicator 328 to display and print out the pressure at which the fluid penetration occurred.

The above-described method of operation shows that the test apparatus 320 allows materials to be tested for moisture penetration resistance without human observation. Consequently, the potential for human error can be reduced thereby yielding more consistent and reproducible test results.

Figure 22:
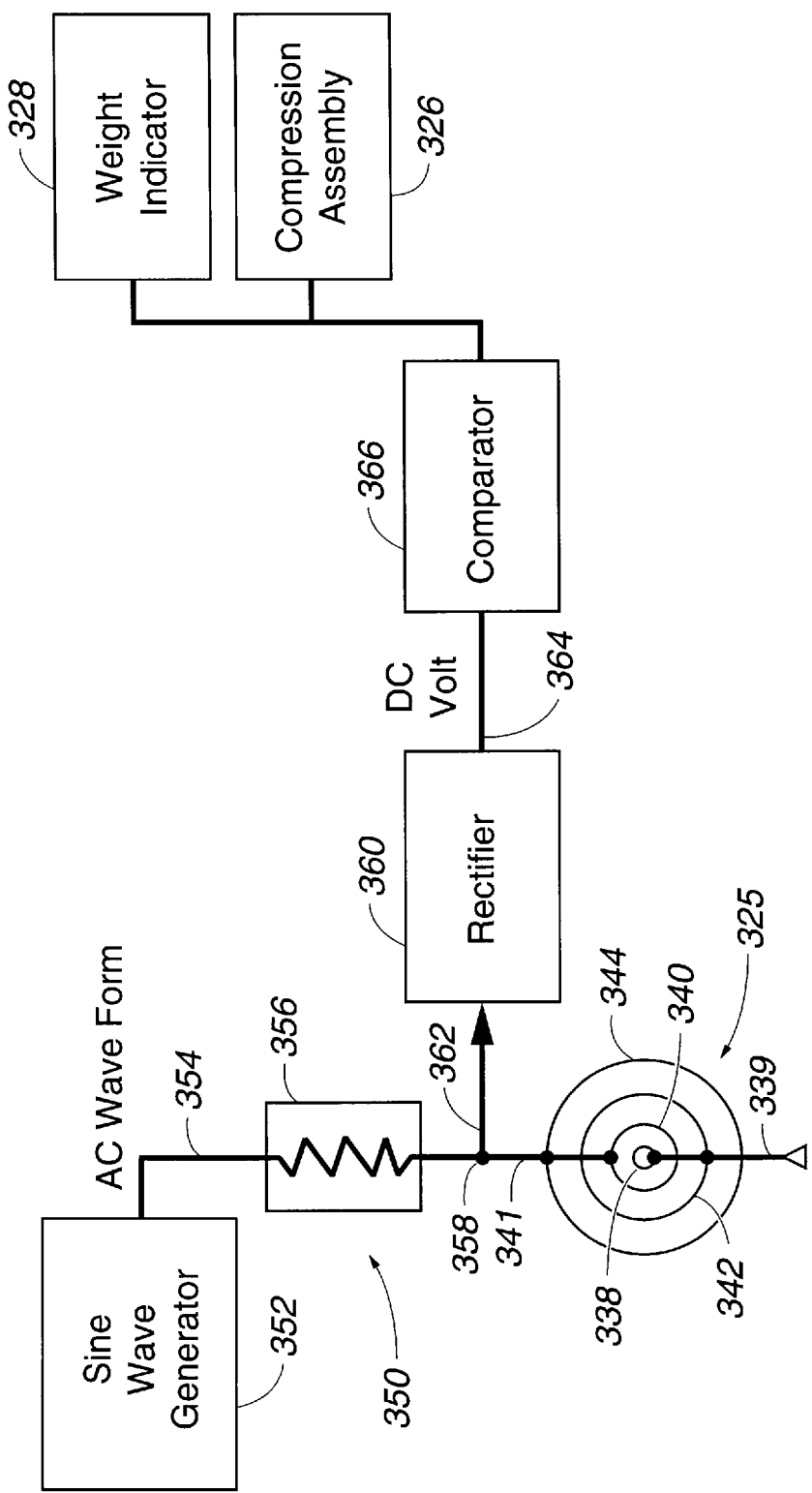
FIG. 22 is a block diagram illustrating control circuit components suitable for use with the universal penetration test apparatus of FIG. 19.

It will be appreciated that the control circuitry could have a variety of conventionally known configurations. FIG. 22 is a block diagram illustrating an exemplary control circuitry component configuration 350 suitable for use in association with the sensor mechanism 325. The control circuitry 350 includes a sine wave generator 352 that produces an AC voltage waveform. Wire 354 directs the waveform across a fixed resistance 356 to node 358. Node 358 is connected to the second and fourth rings 340 and 344 of the sensing mechanism 325 via positive lead 341. The first and third rings 338 and 342 of the sensing mechanism 325 are grounded via negative lead 339.

Node 358 is also connected to a rectifier 360 via wire 362. The rectifier 360 converts the AC voltage to a DC voltage. The DC voltage is directed via wire 364 to a comparator 366 which compares the DC voltage to a predetermined voltage value. If the DC voltage is above the predetermined voltage, no output signals are generated by the comparator 366. However, if the DC voltage falls below the predetermined voltage level, the comparator 366 generates output signals that cause the compression assembly 326 to be deactivated and the weight indicator 328 to print out the pressure being exerted on the material 232.

When there is no leakage of challenge fluid through the material 232, the resistance of the sensing mechanism 325 is infinite (open circuits exist between the rings 338, 340, 342 and 344). Consequently, all of the AC waveform's amplitude passes through the rectifier 360 and is converted into a DC voltage that is higher than the predetermined voltage level. Since the DC voltage is higher than the pre-determined voltage level, no output signals are generated by the comparator 366.

However, if there is leakage through the material 232, the resistance of the sensor mechanism 325 becomes much lower (the fluid reduces the impedance between two or more of the concentric rings 336). This results in the AC waveform being divided between the positive lead 341 and the wire 362. Because the AC waveform is divided, the DC voltage output generated by the rectifier 360 is reduced below the predetermined voltage level (trip level) of the comparator 366. Consequently, the comparator 366 generates the output signal which causes the compression assembly 326 to be deactivated so that no additional pressure is applied to the test material 232 and concurrently causes the weight indicator 328 to display and print out the pressure at which the fluid penetration occurred.

Figure 23:
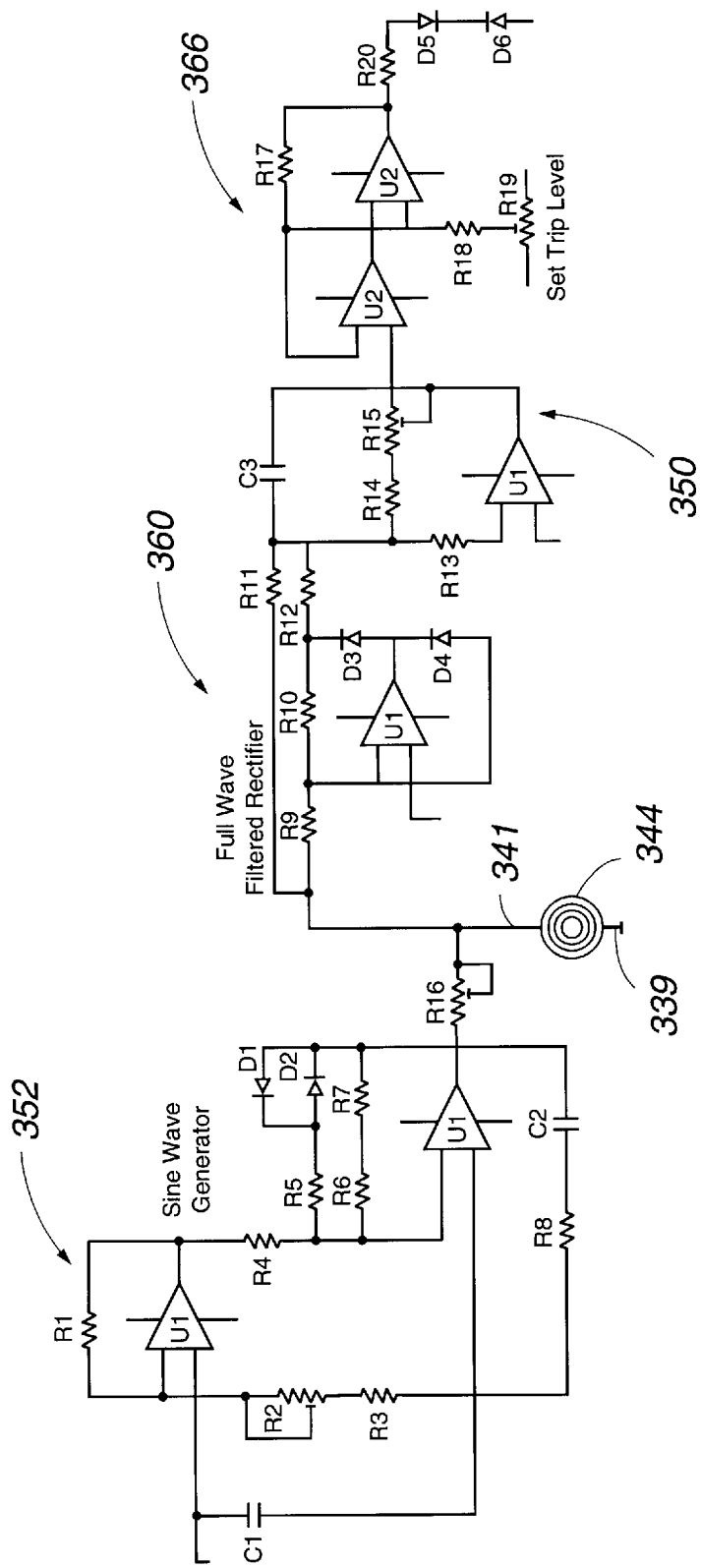
FIG. 23 shows a circuit diagram for exemplary control circuitry suitable for use with the universal penetration test apparatus of FIG. 19.

FIG. 23 is a circuit diagram that illustrates a suitable configuration for the sine wave generator 352, rectifier 360, and comparator 366. However, it will be appreciated that circuit designs for sine wave generators, rectifiers, and comparators are well known in the art. Consequently, the invention is not intended to be limited to the circuit diagram of FIG. 23.

It will be appreciated that the number and spacing of the rings can be varied without departing from the present invention. For example, if desired, only two concentrically spaced rings can be utilized. Additionally, it is not necessary for the conductive material to be configured as concentric rings. Consequently, the present invention includes sensing mechanisms having any type of configuration that includes spaced apart electrical contacts. For example, a test head having a pair of spaced apart linear contacts is one type of alternative configuration.

It is to be understood, however, that even though numerous characteristics and advantages of the present invention have been set forth in the foregoing description, together with details of the structure and function of the invention, the disclosure is illustrative only, and changes may be made, in detail, especially in matters of shape, size and arrangement of parts within the principles of the invention, to the full extent indicated by the broad general meaning of the terms in which the appended claims are expressed.

What is claimed is as follows:

1. A penetration test apparatus for measuring resistance of a material to a challenge fluid comprising:

an absorbent pad capable of absorbing the challenge fluid;

a compression member having a first end;

a compression assembly for compressing the material between the first end of the compression member and the pad; and a sensing mechanism which detects any challenge fluid which penetrates the material;

wherein the sensing mechanism includes first and second spaced apart electrical contacts provided on the first end of the compression member, the first contact being connected to a positive voltage and the second contact being connected to a negative voltage; and wherein the first and second electrical contacts comprise first and second concentric rings of conductive material having different diameters.

2. The test apparatus of claim 1, wherein the sensing mechanism includes a printed circuit board provided on the first end of the compression member.

3. The test apparatus of claim 2, wherein the printed circuit board is adhesively affixed to the first end of the compression member.

4. The test apparatus of claim 2, wherein the sensing mechanism further includes first and second spaced apart electrical contacts provided on the printed circuit board, the first contact being connected to a positive voltage and the second contact being connected to a negative voltage.

5. The test apparatus of claim 4, wherein the first and second electrical contacts comprise first and second concentric rings of conductive material having varying diameters.

6. The test apparatus of claim 2, wherein the sensing mechanism further includes a plurality of spaced concentric rings of conductive material, the concentric rings being alternately connected between a positive and a negative voltage.

7. A universal penetration test apparatus for measuring resistance of a material to a challenge fluid, comprising:

an absorbent pad capable of absorbing the challenge fluid;

a compression member having a first end;

a compression assembly for compressing the material between the first end of the compression member and the pad; and a printed circuit board affixed to the first end of the compression member, the printed circuit board including a plurality of concentric conductive rings having varying diameters and having alternating polarities;

control circuitry electrically connected to the conductive rings, the control circuitry being constructed and arranged to detect a flow of current between any two consecutive conductive rings upon penetration of the challenge fluid through the material, the control circuitry shutting off the compression assembly upon detection of the flow of current whereby the compression assembly no longer compresses the material.

8. The test apparatus of claim 7, further comprising a weighing indicator for measuring and printing out the pressure applied to the material at the time the challenge fluid penetrates the material.

9. A method for measuring resistance of a material to a challenge fluid, comprising:

placing the material adjacent to a pad containing the challenge fluid;

compressing the material against the pad by use of a compression assembly;

using a sensor electrically connected to a control circuit to automatically detect when the challenge fluid penetrates the material, the sensor sending an electrical signal to the control circuit upon detection of the challenge fuid penetrating the material; and the control circuit switching off the compression assembly upon detection of the challenge fluid by the sensor such that the material is no longer compressed.

10. A method in accordance with claim 9, including the step of the control circuit sending a signal to a weight indicator upon detection of the challenge fluid by the sensor such that the force exerted by the compression assembly is recorded.

11. A method in accordance with claim 10, including the step of printing out the force exerted by the compression assembly.

\* \* \* \* \*